(12) United States Patent
Kaeppler et al.

(10) Patent No.: US 7,626,078 B2
(45) Date of Patent: Dec. 1, 2009

(54) **POLYCOMB GENES FROM MAIZE—*MEZ1* AND *MEZ2***

(76) Inventors: Shawn M Kaeppler, 5290 County Highway A, Oregon, WI (US) 53575; Nathan A. Springer, 918 Washington St., Northfield, MN (US) 55057; Timothy G. Helentjaris, 2960 NW. 73rd La., Ankeny, IA (US) 50021; Roland L. Phillips, 819 Tanglewood Dr., Shoreview, MN (US) 55126

( * ) Notice: Subject to any disclaimer, the term of this patent is extended or adjusted under 35 U.S.C. 154(b) by 0 days.

(21) Appl. No.: 12/013,464

(22) Filed: Jan. 13, 2008

(65) Prior Publication Data

US 2008/0155717 A1 Jun. 26, 2008

Related U.S. Application Data

(63) Continuation of application No. 11/633,204, filed on Dec. 4, 2006, now abandoned, which is a continuation of application No. 11/230,145, filed on Sep. 19, 2005, now abandoned, which is a continuation of application No. 09/906,453, filed on Jul. 16, 2001, now abandoned.

(60) Provisional application No. 60/218,745, filed on Jul. 17, 2000.

(51) Int. Cl.
*C12N 15/82* (2006.01)
*C12N 15/29* (2006.01)
*A01H 5/00* (2006.01)
*A01H 5/10* (2006.01)

(52) U.S. Cl. ........................ 800/278; 800/298; 800/295; 800/320.1; 435/252.3; 435/320.1; 435/468; 536/23.6

(58) Field of Classification Search ........................ None
See application file for complete search history.

(56) References Cited

U.S. PATENT DOCUMENTS 5,633,135 A 5/1997 Croce et al.
6,229,064 B1 5/2001 Fischer et al.

FOREIGN PATENT DOCUMENTS

| WO | WO 99/55870 | 4/1999 |
| WO | WO 99/55870 | 11/1999 |
| WO | WO 99/57247 | 11/1999 |
| WO | WO 01/16325 | 3/2001 |

OTHER PUBLICATIONS

Goodrich et al., Nature, 386:44-51 (1997).
Grossniklaus et al., Science, 280:446-450 (1998).
Jones et al., Molecular and Cellular Biology, 18(5):2825-2834 (1998).
Kelly et al., Development, 125:2451-2456 (1998).
Ohad, et al., The Plant Cell, 11:407-415 (1999).
Pirotta, V., Current Opinion in Genetics & Development 7:249-258 (1997).
Pirotta, V., Cell, 93:333-336 (1998).
Preuss, D., The Plant Cell, 11:765-767 (1999).
Spillane, C., et al., Current Biology, 10:1535-1538 (2000).
Simon, J. et al., Mech. Of Devel. 53 (1995) 197-208.
Simon, J., Current Opinion in Cell Biology 1995, 7:376-385.
Sewalt, Richard et al., Molecular and Cellular Biology, Jun. 1998, p. 3586-3595, vol. 18, No. 6.
Roche Siobhan E., et al., Genetics, 149: 1839-1855 (Aug. 1998).
Reijnen, Marlene et al., Mech. Of Devel., 53 (1995) 35-46.
Peterson Aidan, et al., Molecular and Cellular Biology, Nov. 1997, p. 6683-6692, vol. 17, No. 11.
Pal-Bhadra, Manika, et al., Cell, vol. 99, 35-46, Oct. 1, 1999.
Pal-Bhadra, Manika, et al., Cell, vol. 90, 479-490, Aug. 8, 1997.
NG, Joyce, et al., Molecular and Cellular Biology, May 2000, p. 3069-3078, vol. 20, No. 9.
Luo, Ming et al., Proc. Natl. Acad. Sci. USA, vol. 96, pp. 296-301, Jan. 1999.
Lohuizen, Maarten et al., Molecular and Cellular Biology, Jun. 1998, p. 3572-3579, vol. 18, No. 6.
Laible, Gotz et al., The EMBO Journal, vol. 16, No. 11, pp. 3219-3232, 1997.
Korf, Ian et al., Development, 125, 2469-2478 (1998).
Kiyosue, Tomohiro et al., Proc. Natl. Acad, Sci. USA, vol. 96, pp. 4186-4191, Mar. 1999.
Kinoshita, Tetsu et al., The Plant Cell, vol. 11, 1945-1952, Oct. 1999.
Kelly, William G. et al., Development, 125, 2451-2456 (1998).
Jones, Richard S. et al., Molecular and Cellular Biology, Oct. 1993, p. 6357-6366, vol. 13, No. 10.
Jones Richard S. et al., Genetics 126: 185-199 (Sep. 1990).
Holderman, Richard et al., Development 125, 2457-2467 (1998).
Gutjahr, Thomas et al., The EMBO Journal, vol. 14, No. 17, pp. 4296-4306, 1995.
Grossniklaus, Ueli et al., Science, vol. 280, Apr. 17, 1998, pp. 446-450.
Finnegan, E. Jean et al., Proc. Natl. Acad., Sci USA, vol. 93, pp. 8449-8454, Aug. 1996.
Chaudhury, Abdul et al., Proc. Natl. Acad. Sci, USA, vol. 94, pp. 4223-4228, Apr. 1997.
Carrington Elizabeth et al., Development, 122, 4073-4083 (1996).
Bornemann, Douglas et al., Development, 122, 1621-1630 (1996).
Vielle-Calzada, J.P. et al., Genes & Development, 13:2971-2982 (1999).
Bork P., Genome Research., 10:398-400 (2000), "Powers and Pitfalls in Sequence Analysis: The 70% Hurdle".

(Continued)

*Primary Examiner*—Medina A Ibrahim
(74) *Attorney, Agent, or Firm*—Polsinelli Shughart PC

(57) ABSTRACT

The present invention relates to polycomb genes isolated from *Zea mays*, and host cells and plants transformed with a Mez2 gene.

11 Claims, 14 Drawing Sheets

OTHER PUBLICATIONS

Lazar et al., Molecular and Cellular Biology., 8(3): 1247-1252 (1988), "Transforming Growth Factor: Mutation of Aspartic Acid 47 and Leucine 48 Results in Different Biological Activities".

Broun et al., Science., 282:131-133 (1998), Catalytic Plasticity of Fatty Acid Modification Enzymes Underlying Chemical Diversity of Plant Lipids.

Science Compass, Science, vol. 292, pp. 1486-1487, 2001.

Bork. Genome Research, vol. 10, pp. 398-400, 2000.

Lazar et al., Molecular and Cellular Biology, vol. 8(3), pp. 1247-1252, 1988.

Broun et al., Science, vol. 282, pp. 131-133, 1998.

International Search Report Dated Sep. 20, 2002.

FIG. 1A
Mez1 Sequence

```
   1 CGCGTGTGAG GGCGGGAGAG CGCGCGGGGC TAGGGTTTCC GCGGGTGATG
  51 GAAGCAGAGG CTGCCGCGGC GGTAGTGGCG TCGTCCGCAT CTGCCTCGGC
 101 TTCCGCGGGC CGGTCTCGCC CATCTAGCAG CGCCGCCTCG GTCACCAGTA
 151 ATTCGGCTGT GCGAGCTGGA GAAGAAAATG CTGCCTCCCT CTATGTTTTA
 201 TCTGTTATTG ACTCGTTAAA AAAGAGGATT ACCGCAGATC GTTGACTTA
 251 CATTAAGAAT AGGATAGGGG AGAACAAGAC TAATATCAGC AGCTATACAC
 301 AGAGGACTTA CAATTTATCA AAAAATAGGC AAATTAGTAC ATCAAAGGGT
 351 ACTGATTCAG CATCAAATTT GCTCACAAAA AGGCAAGATG ATGCGCTATG
 401 CACCCTGCAT AGTCTTGATA TTATTCCGGT TGACAAAGAT GGTGGCACTT
 451 TTCAAGACGA AAGTCCTTTC TCTTCATCTA ATGTTATGTT TGGTCGAAAT
 501 CTTGGTCCCA AGAATGCTAT TATTAGACCA ATTAAACTAC CAGAAGTGCC
 551 AAAGCTTCCA CCTTATACAA CATGGATATT TTTGGACAGG AACCAAAGGA
 601 TGACAGAAGA CCAATCTGTA CTTGGTCGAC GGAGGATTTA CTATGATACC
 651 AGTTGTGGTG AAGCTCTAAT TTGCAGTGAT AGTGAAGATG AAGCCATTGA
 701 AGATGAGGAG GAAAAAAAGG AATTTAAACA TTCTGAAGAT CACATTATTC
 751 GGATGACAGT TCAAGAATGT GGCATGTCTG ATGCTGTACT GCAAACGCTA
 801 GCTCGACACA TGGAGCGGGC TGCTGATGAC ATAAAGGCCA GGTATGAAAT
 851 TCTGCATGGT GAGAAAACTA AGGATTCTTG CAAGAAAGGG ACTGAGCATA
 901 ATGTCAAAGT GGAAGATTTG TACTGTGACA AAGATTTGGA TGCAGCATTG
 951 GATTCTTTTG ACAATCTCTT CTGTCGACGA TGTCTAGTGT TTGATTGCAA
1001 GCTACATGGG TGTTCTCAAG ATTTAGTATT TCCTCCAGAA AAACAACCAG
1051 CTTGGAGGGG CGTTGATGAC AGTGTACCCT GTGGTATTCA TTCCCATAAA
1101 CTGGCATCTG AACCAGATTC TGCTGCTGGT GCTGATCCCA TGCTTTTTGA
1151 TGTTGAGGAG CCAACTCACT CATCAGACAA TGTGATGAAC CAGCCAGGTT
1201 CAAATAGGAA AAAGAACGGC TCCAGTGGAA GGAAGACTAA ATCTCAACAA
1251 AGTGAAAGCT CTTCAACTGC AAGAGTTATC TCAGAAAGCA GTGCTTCGGA
1301 AGTACATCCA ATAAGCAATA AATCTCCACA ACACTCCCCT AGTCCCTCAA
1351 AAGTTAAAAT TGGGCCAAAA GGTGGAATCA GAAAGATTAC CAATAGACGA
1401 ATCGCTGAGA GAATTCTTAT GAGTGTGAAG AAAGGACAAA GGGAAATGGC
1451 ATCATCTGAT TCTAATTTTG TTAGTGGATA TCTTTTGGCA AGGGACATGA
1501 AGCTTAGGTC TGATACACGA AATGGAAATA AGGAATTAAT TGTATCCTCA
1551 CAACAGAGTT CTCCAAGCAC AAGAAGTTCC AAAAAGAAGA GTACACCTCA
1601 AATTGGGAAC AGCTCAGCTT TGCTGAGGC TCATAATGAT TCAACAGAGG
1651 AAGCAAATAA CCGTCATTCA GCAACAGATG GTTACGATAG TTCAAGGAAA
1701 GAAGAATTCG TCAATGAGAA TTTATGCAAG CAGGAGGTGT ACTTGAGATC
1751 ATGGAAGGCA ATTGAGCAGG GACTTCTTGT GAAAGGATTA GAGATTTTTG
1801 GAAGGAACAG TTGTTTAATT GCTCGGAACC TTCTTGGTGG AATGAAGACG
1851 TGCAAAGATG TTTTTCAATA TATGAATTAT ATTGAAAACA ACAGTGCCTC
1901 TGGAGCTCTT AGTGGTGTTG ATTCTCTTGT CAAAGGATAT ATTAAGGGTA
1951 CTGAGTTGCG CACAAGATCA AGATATTTTA GAAGGCGAGG TAAAGTCCGT
2001 CGTTTGAAGT ACACCTGGAA ATCTGCAGGT TACAATTTCA AAAGGATTAC
2051 CGAAAGGAAG GATCAGCCTT GTCGACAATA TAATCCTTGT GGTTGTCAAT
2101 CTACATGCGG AAAGCAGTGT CCATGTCTTT CAAATGGGAC ATGTTGTGAG
2151 AAATACTGTG GGTGTCCAAA AATTTGCAAG AATCGTTTTC GAGGATGTCA
2201 CTTGTGCAAG AGCCAGTGTC GCAGCCGCCA ATGTCCATGT TTTGCAGCTG
2401 CAGATGTCTC TGGCTGGGGA GCATTCCTCA AGAATAGTGT TAGCAAACAT
2451 GAATACCTTG GTGAGTACAC TGGGGAACTA ATCTCACACA AGAAGCAGA
2501 TAAGCGTGGA AAGATATATG ATCGTGAGAA CTCATCGTTC CTTTTCAACC
2551 TGAACAACGA GTATGTTCTT GACGCATACA GAATGGGTGA CAAGCTGAAA
```

FIG. 1A-1

```
2601 TTTGCCAACC ATGCCCCTGA CCCGAATTGC TATGCCAAGG TTATCATGGT
2651 AACTGGTGAT CATAGAGTGG GCATATTCGC CAAAGAAAGA ATCCTCGCTG
2701 GTGAAGAGTT ATTCTACGAT TACCGCTATG AGCCTGACAG AGCCCCTGCT
2751 TGGGCCCGTA AGCCTGAGGC GTCGGGAGCA AAGGATGATG GGCAACCGTT
2801 CAATGGGCGT GCAAGAAGC TCGCCCAAAA CAACAGAGGC TGAATCTGAT
2851 TTGATTCTTT CATTGTTAGG ACAAATTTGG CAGCCATTCA ACTAATATAA
2901 GGAACCTGTC ATTCATAGGC CCAATTTAT TTGAACTCGT CATTGTAACT
2951 CGTATGTGCT TGAATTCTCC ATGGCAGCTG GTCCTGCCAT CCGTAGAGTT
3001 AGGTCCCGTT TGTTTTGAGG AACTAAAAAT TAATCCCTCT ATTTTAGTCA
3051 CATTGAGTCT TAGATTGTTA AACGGCGGGA CTAAAACAAA AGACTAAACT
3101 ATTTGTCTCT AGTACCTCAA GCCATGACTA AAAGGGAATA AATCATATAA
3151 ATTTTATTTT TATCCTTCCT TTAAAAAAAA
```

FIG. 1B

```
  1  MEAEAAAAVV ASSASASASA GRSRPSSSAA SVTSNSAVRA GEENAASLYV
 51  LSVIDSLKKR ITADRLTYIK NRIGENKTNI SSYTQRTYNL SKNRQISTSK
101  GTDSASNLLT KRQDDALCTL HSLDIIPVDK DGGTFQDESP FSSSNVMFGG
151  NLGPKNAIIR PIKLPEVPKL PPYTTWIFLD RNQRMTEDQS VLGRRRIYYD
201  TSCGEALICS DSEDEAIEDE EEKKEFKHSE DHIIRMTVQE CGMSDAVLQT
251  LARHMERAAD DIKARYEILH GEKTKDSCKK GTEHNVKVED LYCDKDLDAA
301  LDSFDNLFCR RCLVFDCKLH GCSQDLVFPP EKQPAWRGVD DSVPCGIHSH
351  KLASEPDSAA GADPMLFDVE EPTHSSDNVM NQPGSNRKKN GSSGRKTKSQ
401  QSESSSTARV ISESSASEVH PISNKSPQHS PSPSKVKIGP KGGIRKITNR
451  RIAERILMSV KKGQREMASS DSNFVSGYLL ARDMKLRSDT RNGNKELIVS
501  SQQSSPSTRS SKKKSTPQIG NSSAFAEAHN DSTEEANNRH SATDGYDSSR
551  KEEFVNENLC KQEVYLRSWK AIEQGLLVKG LEIFGRNSCL IARNLLGGMK
601  TCKDVFQYMN YIENNSASGA LSGVDSLVKG YIKGTELRTR SRYFRRRGKV
651  RRLKYTWKSA GYNFKRITER KDQPCRQYNP CGCQSTCGKQ CPCLSNGTCC
701  EKYCGCPKIC KNRFRGCHLC KSQCRSRQCP CFAADRECDP DVCRNCWVGC
751  GDGTLGVPNQ RGDNYECRNM KLLLKQQQRV LLGRSDVSGW GAFLKNSVSK
801  HEYLGEYTGE LISHKEADKR GKIYDRENSS FLFNLNNEYV LDAYRMGDKL
851  KFANHAPDPN CYAKVIMVTG DHRVGIFAKE RILAGEELFY DYRYEPDRAP
901     ARKPEASG AKDDGQPFNG RAKKLAQNNR G*
```

FIG. 2A-1

```
   1  CCGTCGCAGA  ATTCGCGCCA  CCGCCCGCGA  TGGCTTCGTC  CTCGAAGGCC
  51  TCCGATTCCT  CCCAACGATC  CAAGCGGTCG  GATCAGGGGA  TGGGCAAGGA
 101  CGCCGCTGCC  GCCTCTGTTG  TCCCGATCCA  CGCGAACCTG  ACGCAGCTGA
 151  TACGGCAAGT  CCAATCGGGG  CGCCTCGCGT  ACATCAAGGA  GAAATTGGAG
 201  GTGAACAGGA  AAACGCTGCA  GAGGCACTCC  TGCTCGCTGT  TCGACGTGGC
 251  AGCGGCGGCG  GAGGTGGCGT  CGAGGGGCAC  CGATGGCGGC  AACGCGCTGT
 301  CACAGCGCGC  GGCGGAGAGA  CAGTGTGGGT  CAGACCTGGC  AAACGGGATA
 351  GGGGAGAGGG  ATGTGGTTTC  CGTTCACGAG  GAGAACCTGG  CTACCGGTAC
 401  GCTCGCGCTC  TCCAGCTCGG  GCGCTACCGC  GCAGCGGACA  ATTGTGCGGT
 451  TCGTGAAGCT  GCCGCTGGTT  GAGAAGATCC  CTCCGTACAC  CACTTGGATC
 501  TTCCTGGACA  AAAACCAAAG  AATGGCTGAC  GATCAGTCAG  TTGTTGGTAG
 551  GAGAAGGATA  TACTATGATA  CAGTTGGAAA  CGAGGCTCTG  ATCTGCAGTG
 601  ACAGTGATGA  AGAAATTCCA  GAACCAGAGG  AAGAGAAACA  CTTTTTCACA
 651  AAGGGAGAAG  ATCATTTGAT  ATGGAGAGCT  ACTCAAGACC  ATGGGTTAAA
 701  CCAAGAGGTT  GTTAATGTCC  TTTGCCAGTT  TATTGGTGCA  ACCCCATCAG
 751  AAATTGAGGA  AGATCTGAA  GTCCTATTTG  AGAAAAATGA  GAAGCACTCA
 801  GGATCTTCAG  ATAAGATAGA  GAGCCGACTT  TCTCTTGACA  AAACTATGGA
 851  TGCCGTTCTG  GATTCTTTTG  ATAATCTCTT  CTGCCGCAGA  TGCTTGGTTT
 901  TTGATTGCCG  CCTTCATGGT  TGTTCACAGA  ATTTGGTATT  CCATGTGAG
 951  AAGCAACCCT  ACAGCTTTGA  CCCTGATGAA  ACAAGAAGC   CATGTGGTCA
1001  TTTGTGCTAC  CTTCGATTTC  CCCAGTGGAG  AGAAGGATTT  AAAG^GATGC
```

FIG. 2A-2

```
1051    ATGATGATGG TCTTGCTGGT GGTGCAACAT ATACTATGGA ATCGGGAACT

1101    GCCTCACAGA GAGTTGATGT TAATGTTATG TATGAATCAG AAGATTCAAA

1151    CCGACAGAAA GGCAACATTA GGTCCATGAC ACTAGTTGGA ACCAGTGGAC

1201    CAAAAATAAT TTCTTCTGTC AGTGCGGAAG AAAGCACTAC TACTCCAGCA

1251    GATATCTCTG AAACAGAGAA TGTATCCTCT GATTTGCCTC CCAGTAGTTT

1301    AAGGAAACAC AAGATTTCAA ACATGGACC TAGGTACAGG GAGCATTCTC

1351    CTGGCAAAAG GCAGAAGGTT TTCACTTCTG ACATTTCTTT TGAAGGCAGT

1401    ATAATGAATA AACTTTCCAT TCCGGAGATT CGTGACACAA GACTAGAGTC

1451    CAGAGAATCT GGTGGTGATA AACTACGAAT TCTTGACGAG TCCACTAAGA

1501    AGACTTCAAG GAAAGATATG TGTGGGGAAA GCCCAGCTAC TACCATGGAA

1551    AATGTGGGAA GACAGAGTAA TAAAGTGTAT TCAACAAAGA ATTTCTTGGA
                                        ▲Mez2-Mu4
1601    GTCCACTCTT TCTTGTTGGA GTGCCTTAGA GCGAGATCTA TACTTGAAGG

1651    GCATAGAGAT ATTTGGAAAG AACAGCTGTC TCATCGCCAG AAACTTACTA

1701    TCTGGTCTTA AGACCTGCAT AGAAGTGGCA AACTACATGT ATAACAATGG

1751    TGCAGCGATG GCGAAGAGAC CTCTCTTGAA TAAATCCATC TCAGGCGACT

1801    TTGCAGAAAA TGAACAAGAC TACATGGAGC AAGACATGGC TGCCAGAACA

1851    AGAATCTATC GTCGGAGGGG CCGCAATCGA AGCTGAAAT ATACTTGGAA

1901    ATCTGCAGGG CATCCAACTG TTAGAAAAAG AACTGATGAC GGGAAGCAAT

1951    GTTACACACA ATATAGCCCA TGTGCGTGCC AGCAAATGTG TGGTAAAGAT

2001    TGCCCCTGTG CGGACAAGGG AACTTGCTGT GAGAAGTACT GTGGGTGTTC
```

FIG. 2A-3

```
                                        ▽VIntron 1
2051  GAAGAGCTGC AAAAACAAGT TTAGAGGCTG TCATTGTGCA AAAAGCCAAT
                                 ▲Mez2-Mu1

2101  GCAGAAGCAG ACAGTGCCCC TGTTTTGCAG CCAGTCGTGA ATGTGATCCA

2151  GATGTTTGTA GGAATTGCTG GGTGAGCTGT GGAGATGGTT CACTAGGTG
                                ▲Mez2-Mu2

2201  GCCACTTGCA AGAGGTGATG GTTATCAGTG TGGAAATATG AAGCTCCTTT
              Mez2-Mu3A▲
                            ▽ Intron 2
2251  TGAAACAACA GCAAAGGATT TTGTTAGGAA GATCTGATGT TGCAGGTTGG ▽VIntron 3
2301  GGTGCATTCA TTAAGAATCC TGTAAATAAA AATGATTATC TTGGAGAATA 2351  TACTGGTGAA TTGATCTCTC ACAAGGAAGC AGACAAACGC GGCAAAATTT
                                                   ▽Bntron 4
2401  ATGACCGGGC AAACTCATCT TTTCTGTTCG ATTTAAATGA CCAGTATGTG 2451  TTGGATGCTT ATCGCAAGGG GGACAAATTG AAGTTCGCAA ATCACTCATC
                           ▽VIntron 5
2501  TAACCCCAAC TGCTATGCAA AGGTGATGCT GGTGGCTGGC GACCATCGGG

2551  TTGGTATATA TGCGAAGGAG CATATTGAGG CTAGCGAGGA ACTCTTTTAT

2601  GATTATCGTT ATGGACCTGA CCAGGCTCCG GCTTGGGCTA GGAGACCCGA

2651  AGGATCAAAG AAGGACGAGG CATCCTTCTC TCACCGTCGA GCACACAAAG

2701  TGGCTCGATA GCTGAAGAGT CGCTCCGGAT GATACAATAT GCAGTAAACT

2751  TAATACTTAA TACATGATTC AGTCCTAGTT CATTGGTAGA TAAACATGCT

2801  ATATACTATC CATTAGTAAA TAAACTCTCA TTCATCGAGT TGGAGAATAA

2851  ATGCGTATAA ACATATGTGG ACCTCAGGTC GGGAAGGTGG CAACCTTGTT

2901  AGTTTGAGCA CCAACAGGTT CTCAAACTTG AGTGGCTATT GCTAGAGTAT

2951  CAAATAATGG CTGCGACTAT AGCCTTGTTT GTATATTTTC TTGGTGAGAT

3001  GAAATAATTT GTCAAATGTA CACTTAAAAA
```

FIG. 2B

```
  1    MASSSKASDS  SQRSKRSDQG  MGKDAAAASV  VPIHANLTQL  IRQVQSGRLA
 51    YIKEKLEVNR  KTLQRHSCSL  FDVAAAAEVA  SRGTDGGNAL  SQRAAERQCG
101    SDLANGIGER  DVVSVHEENL  ATGTLALSSS  GATAQRTIVR  FVKLPLVEKI
151    PPYTTWIFLD  KNQRMADDQS  VVGRRRIYYD  TVGNEALICS  DSDEEIPEPE
201    EEKHFFTKGE  DHLIWRATQD  HGLNQEVVNV  LCQFIGATPS  EIEERSEVLF
251    EKNEKHSGSS  DKIESRLSLD  KTMDAVLDSF  DNLFCRRCLV  FDCRLHGCSQ
301    NLVFPCEKQP  YSFDPDENKK  PCGHLCYLRF  PQWREGFKEM  HDDGLAGGAT
351    YTMESGTASQ  RVDVNVMYES  EDSNRQKGNI  RSMTLVGTSG  PKIISSVSAE
401    ESTTTPADIS  ETENVSSDLP  PSSLRKHKIS  KHGPRYREHS  PGKRQKVFTS
451    DISFEGSIMN  KLSIPEIRDT  RLESRESGGD  KLRILDESTK  KTSRKDMCGE
501    SPATTMENVG  RQSNKVYSTK  NFLESTLSCW  SALERDLYLK  GIEIFGKNSC
551    LIARNLLSGL  KTCIEVANYM  YNNGAAMAKR  PLLNKSISGD  FAENEQDYME
601    QDMAARTRIY  RRRGRNRKLK  YTWKSAGHPT  VRKRTDDGKQ  CYTQYSPCAC
651    QQMCGKDCPC  ADKGTCCEKY  CGCSKSCKNK  FRGCHCAKSQ  CRSRQCPCFA
701    ASRECDPDVC  RNCWVSCGDG  SLGEPLARGD  GYQCGNMKLL  LKQQQRILLG
751    RSDVAGWGAF  IKNPVNKNDY  LGEYTGELIS  HKEADKRGKI  YDRANSSFLF
801    DLNDQYVLDA  YRKGDKLKFA  NHSSNPNCYA  KVMLVAGDHR  VGIYAKEHIE
851    ASEELFYDYR  YGPDQAPAWA  RRPEGSKKDE  ASFSHRRAHK  VAR*
```

FIG. 3

A. Alignment of amino acid sequence of MEZ1 and MEZ2.

```
Mez1    1  MEAEAAAAVVASSASASASAGRSRPSSSAASVTSNSAVRAGEENAASLYVLSVIDSLKKR
Mez2    1  ---------MASSSKASDSSQRSK--------RSDQGMGKDAAAASVVPIHANLTQLIRQ

Mez1   61  ITADRLTYIKNRIGENKTNISSYTQRTYNLSKNRQISTSKGTDSASNLLTKRQDDALCTL
Mez2   44  VQSGRLAYIKEKLEVNRKTLQRHSCSLFDVAAAAEVASRG---TDGGNALSQRAAERQCGS

Mez1  121  HSLDIIPVDKDGGTFQDESPFSSSNVMFGGNLGPKNAITRPIKLPEVPKLPPYTTWIFLD
Mez2  102  DLANGIGE-RDVVSVHEENLATGTLALSSSGATAQRTIVRFVKLPLVEKIPPYTTWIFLD

Mez1  181  RNQRMTEDQSVLGRRRIYYDTSCGEALICSDSEDEAIEDEEEKKEFKHSEDHIIRMTVQE
Mez2  161  KNQRMADDQSVVGRRRIYYDTVGNEALICSDSDEEIPEPEEEKFFTKGEDHLIWRATQD

Mez1  241  CGFSDAVLQTLARHMERAADDIKARYELLHGEKTKDSCKKGTEHNVKVEDLYCDKDLDAA
Mez2  221  HGLNQEVMIVLCQFIGATPSEIEERSEVLFEKNEKHSGSS---D-KIESRLSLDKTMDAV

Mez1  301  LDSFDNLFCRRCLVFDCKLHGCSQDLVFPPEKQPAWRGVDISVPCGIHSHKLAS----EP
Mez2  277  LDSFDNLFCRRCLVFDCRLHGCSQNLVFPCEKQPYSFDPDENKKPCGHLCYLRFPQWREG

Mez1  357  DSAAGADPLLFDVEEPTHSSDNVMNQPGSNRKKNGSSGRKTKSQQSESSSTARVISESSA
Mez2  337  FKEMHDDGLAGGATYTMESGTASQRVDVNVMYESEDSNRQKGNIRSMTLVGTSGPKIISS

Mez1  417  SEVHPISNKSPQHSPSPSKVKIGPKGGLRKITNRRIAERILMSVKKGQREMASSDSNEVS
Mez2  397  VSAEESHTTPADISETENVSSDLPPSSLRKHKISKHGPRYREHSPGKRQKVFISDISFEG

Mez1  477  GYILARDMKLRSDTRNGNKELIVSSQQSSPSIRSSKKKSTPQIGNSSAFAEAHNDSTEEA
Mez2  457  SILNKLSIPEIRDTRLE--------------SRESGGDKLRILDES--TKKTS---RKDM

Mez1  537  NNFHSATDGYDSSRKEEFVNENLCKQEVYLRSMKALEQGLLVKGLEIFGRNSCLIARNLL
Mez2  498  CGESPATTMENVGRQSNKVYSTKNFLESTLSCWSALERDLYLKGLEIFGKNSCLIARNLL

Mez1  597  GGLKTCKDVFQYMN-----YIENNSASGALSGVDSLVKGYIKGTELRTRSRYERRRGKVR
Mez2  558  SGLKTCIEVANYMYNNGAAMAKRPLLNKSTSGDFAENEQDYMEQDMAARIRIYRRRGRNR

Mez1  652  RLKYTWKSAGYNFKRITERKDQPCR-QYNPCHCQSTCGKQCPCLSNGTCCEKYCGCPKIC
Mez2  618  KLKITWKSAGHPTVRKRTDDGKQCYTQYSPCACQQMCGKDCPCADKGTCCEKYCGCSKSC

Mez1  711  KNIFRGCHLCKSQCRSRQCPCFAADRECDPDVCRNCWVGCGDGTLGVPNQRGDNYECRNM
Mez2  678  KNL RGCHCAKSQCRSRQCPCFAASRECDPDVCRNCWVSCGDGSLGEPLARGDGYQCGNM

Mez1  771  KLLKQQQRVLLGRSDVSGWGAFLKNSVSKHHYLGEYTGELISHKEADKRGKIYDRENSS
Mez2  738  KLLKQQQRILLGRSDVAGWGAFIKNPVNKNDYLGEYTGELISHKEADKRGKIYDRANSS

Mez1  831  FLLINNEYVLDAYRMGDKLKFANHAPDPNCYAKVIMVTGDHRVGIFAKERILAGEELFY
Mez2  798  FLL NDQYVLDAYRKGDKLKFANHSSNPNCYAKVMLVAGDHRVGIYAKEHIEASEELFY

Mez1  891  DY EPDRAPAWARKPEASGAKDDGQPFNGRAKKLAQNNRG
Mez2  858  D   PDQAPAWARRPEGS-KKDEASFSHRRAHKVAR----
```

FIG. 4
Alignment of E(z) homologs

FIG. 4(cont)
Alignment of E(z) homologs

```
Mez2   354 ESGLASQRVDVNMYESDSNRQK---GNIRSMTLGUSGSKIISSVAEESTTTPSADISETENVSSDLPPSSLRKHKISKHGPEYREHSPGKRQKVFT
EZA1   335 EECSRAVSSDVPHAEASGVSLQVE---KIDIGIKNVDSSSGVQEEHGIRGKKREVPILKDSNDLPNLSNKQKTAASDTKMSFVN-----SVPSLDQALDS
Mez1   377 DNVMNQPGSNRKKNCSSGRKTKSQQSESESTARVISESSAGEVHPISNKSPQHSPSPSKVKIGPKGGIEKITNRRIAERILMSVKKGQREMASSDSNFVS
clf    345 GTKETPTKFSSKLNCRKPKEFPSE--SASSNEKCAIETSDSENGLQQDTNSDKVSSSPKVAGSGRRVGRKRNNNRVAERVPRKTQKROKKTEASDSDSIA
MEDEA  337 DPNN-------------------------------------------------------------------------------------
E(z)   395 SEDS-------------N-------------------------------------------------------------DSMSQFSN SANT***
Mez2   451 SDISFEGNIMNKESIPELRDTRIESRESCGOKLRILDESTKKTSRKDICESPATTMENVGRQSNKVSSTKNFL------ESTLSCWSAFERD
EZA1   427 TKGDQGGTTDNKWNRDSEADAKEVGEPIPDNSVHDGGSSICQPHGSGNGAIIIAEMSEFSRPS---------------TEWNPIEKE
Mez1   477 GYLLARDMKLRSDTRNGNKELIVSQQSPSTRSSKKKSTPQIGNSSAFAEAHNDSTEAANNRHSATDGYDSSRKEEFVNENLCK-QEVYLRSWKAEEQG
clf    443 SGSCSPSDAKHKDNEDATSSSQKHVK-SENGSKRKNGIPAEVSNNSWKDEVPVCQSNEVASELDAPGSDESLRKEEFMGETVSRGRLATNKIMRPHEKS
MEDEA  341 ------------------------------------------------------------------------------TWNIEMEKD
E(z)   408 KDFNHENSKDNGEEVNSAAVAEINSIMAG----------MMNITS---------------------------------TQCVEHGADQA SANT domain*******************                         NLS*********************************
Mez2   538 LYLKGEIFGKNSCLIARNLLSGLKTCEHEVANYKYNEG-AAEAKRPLLNKSISGDFAENEQDYMEQDMAARHITRREFGRNRLKYTWKSAGHPTVRKRT
EZA1   500 LYLKGWEIFGRNSCLIARNLLSGLKTCLEDYSNYMRENE-VSVFRRSSTPN-LLLDDGRTDPGNDNDEVPPRIRLERRHGKTRELKYETKSAGHPSVWKRI
Mez1   576 ILLKGIEIFGRNSCLIARNLLSGLKTCKDYEFQYMNYIENNSASGALSGVDS-------LVACYKGTEHRTRSFYERRFGKVRRLKYTWKSAGYN---FKRI
clf    542 LEDRKGYEIFGMNSCLIARNLLSGFKSGWEVFGYMYTCSENKASFFGGDGLNPDGSSKFDINENVVNNQVRRRSRFLRRRGKVRSRIP-----RKRI
MEDEA  350 LYLKGEIFGRNSDAALMILRGLKTCEHLKNYMREQDCELSLDNKTT------QRHNQVTKKVSRKSSSVREKSRIR----KYARYEPALKT
E(z)   454 LYRVLHKWELKNYCALAANIEH--KTCRQWMEEAQKEE--------------AEFSFEDIRQDFTPPRKKKKQR------LWSLHCRKIQLK
                                                                                                         *********
                  Cys-rich region********************************************************************************
Mez2   637 DECK--QCYTQYSPCAEO-QMCGKDCPCADKGTCCEKYCGCSKSKNKFERGCHCAKSQCHSRQCPCFAASRECDPDVCRNCTVSCGDSLGEPLARGDGYQ
EZA1   598 AGGKNQSCKQYTPCCLL-SMCGKDCPCIANETCCEKYEGCSKSCKNRFRGCHCAKSQCRSRQCPCFAAGRECDPDVCRNCTVSCGDSLGEAPRRCEG-Q
Mez1   668 TERKDCPCRQYNPCGCG--STCGKQCPCLESNGTCCEKYCGPKICENRERGCHLCRSCKNRFERGCHCAKSQCRSRQCPCFAADRECDPDVCRNCWVGGCDHLCVNQRGDNYE
clf    642 LERKDOPCRQFENPCNCQ--IACGKECPCLLNGTCYEKYCGGCPCLTHENCCEKYCGNCAIGQCTNRQCPCFAANRECDPDICRSCPLSCGDHLC----ETPVGIQ
MEDEA  437 TSEAKFYNHYTPCTCK--SKCGQCPCLTHENCCEKYCGEKELNECCSDCNNRFGGNCAIGQCTNRQCPCFECHCA--QGNFRQCPCIAVRECDPDICQACGADQFKLIKIT
E(z)   525 KESSSMHVYMWTPCDHPGHPCDMNQSHQTONFCEKEENCSSDCONRFPGCNC----
```

FIG. 4(cont)
Alignment of E(z) homologs

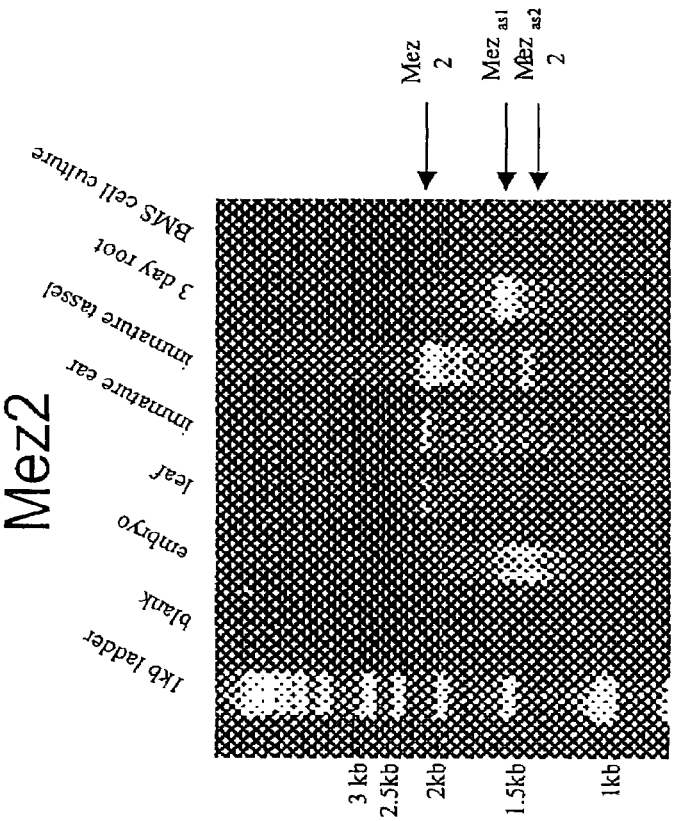
FIG. 8A Mez1
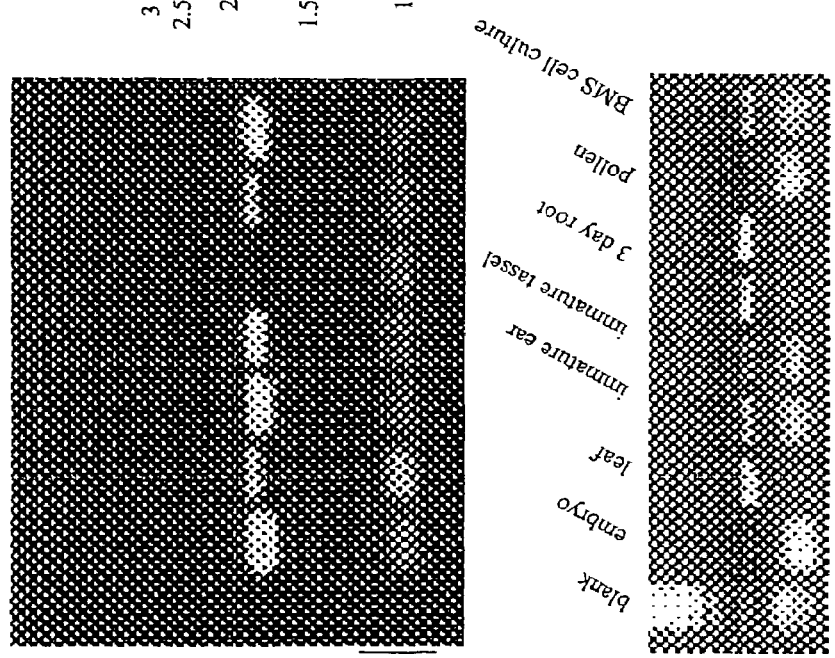
FIG. 8B Mez2

SEQUENCE LISTING

<160> NUMBER OF SEQ ID NOS: 20

<210> SEQ ID NO 1
<211> LENGTH: 3180
<212> TYPE: DNA
<213> ORGANISM: Zea mays

-continued

```
<400> SEQUENCE: 1
cgcgtgtgag ggcgggagag cgcgcggggc tagggtttcc gcgggtgatg gaagcagagg      60
ctgccgcggc ggtagtggcg tcgtccgcat ctgcctcggc ttccgcgggc cggtctcgcc     120
catctagcag cgccgcctcg gtcaccagta attcggctgt gcgagctgga gaagaaaatg     180
ctgcctccct ctatgtttta tctgttattg actcgttaaa aaagaggatt accgcagatc     240
gtttgactta cattaagaat aggatagggg agaacaagac taatatcagc agctatacac     300
agaggactta caatttatca aaaataggc aaattagtac atcaaagggt actgattcag      360
catcaaattt gctcacaaaa aggcaagatg atgcgctatg caccctgcat agtcttgata     420
ttattccggt tgacaaagat ggtggcactt ttcaagacga aagtcctttc tcttcatcta     480
atgttatgtt tggtggaaat cttggtccca agaatgctat tattagacca attaaactac     540
cagaagtgcc aaagcttcca ccttatacaa catggatatt tttggacagg aaccaaagga     600
tgacagaaga ccaatctgta cttggtcgac ggaggattta ctatgatacc agttgtggtg     660
aagctctaat ttgcagtgat agtgaagatg aagccattga agatgaggag gaaaaaaagg     720
aatttaaaca ttctgaagat cacattattc ggatgacagt tcaagaatgt ggcatgtctg     780
atgctgtact gcaaacgcta gctcgacaca tggagcgggc tgctgatgac ataaaggcca     840
ggtatgaaat tctgcatggt gagaaaacta aggattcttg caagaaaggg actgagcata     900
atgtcaaagt ggaagatttg tactgtgaca agatttgga tgcagcattg gattcttttg      960
acaatctctt ctgtcgacga tgtctagtgt ttgattgcaa gctacatggg tgttctcaag    1020
atttagtatt tcctccagaa aaacaaccag cttggagggg cgttgatgac agtgtaccct    1080
gtggtattca ttcccataaa ctggcatctg aaccagattc tgctgctggt gctgatccca    1140 tgcttttga  tgttgaggag ccaactcact catcagacaa tgtgatgaac cagccaggtt    1200
caaataggaa aaagaacggc tccagtggaa ggaagactaa atctcaacaa agtgaaagct    1260
cttcaactgc aagagttatc tcagaaagca gtgcttcgga agtacatcca ataagcaata    1320
aatctccaca cactcccct agtccctcaa aagttaaaat tgggccaaaa ggtggaatca     1380
gaaagattac caatagacga atcgctgaga gaattcttat gagtgtgaag aaaggacaaa    1440
gggaaatggc atcatctgat tctaattttg ttagtggata tcttttggca agggacatga    1500
agcttaggtc tgatacacga aatggaaata aggaattaat tgtatcctca aacagagtt     1560 ctccaagcac aagaagttcc aaaaagaaga gtacacctca aattgggaac agctcagctt    1620
ttgctgaggc tcataatgat tcaacagagg aagcaaataa ccgtcattca gcaacagatg    1680
gttacgatag ttcaaggaaa gaagaattcg tcaatgagaa tttatgcaag caggaggtgt    1740
acttgagatc atggaaggca attgagcagg acttcttgt gaaaggatta gagattttg     1800 gaaggaacag ttgtttaatt gctcggaacc ttcttggtgg aatgaagacg tgcaaagatg    1860
tttttcaata tatgaattat attgaaaaca acagtgcctc tggagctctt agtggtgttg    1920
attctcttgt caaaggatat attaagggta ctgagttgcg cacaagatca agatattta     1980 gaaggcgagg taaagtccgt cgtttgaagt acacctggaa atctgcaggt tacaatttca    2040
aaaggattac cgaaggaag gatcagcctt gtcgacaata taatccttgt ggttgtcaat    2100
ctacatgcgg aaagcagtgt ccatgtcttt caaatgggac atgttgtgag aaatactgtg    2160
ggtgtccaaa aatttgcaag aatcgttttc gaggatgtca cttgtgcaag agccagtgtc    2220
gcagccgcca atgtccatgt tttgcagctg acagggaatg cgatccggat gtttgcagaa    2280
actgttgggt tgggtgtggt gatggtacat tgggagttcc aaaccagaga ggagataatt    2340
```

```
atgaatgccg aacatgaaa ctgcttctta acaacaaca aagggtctta cttggaagat   2400
cagatgtctc tggctgggga gcattcctca agaatagtgt tagcaaacat gaataccttg   2460
gtgagtacac tgggaacta atctcacaca agaagcaga taagcgtgga aagatatatg   2520
atcgtgagaa ctcatcgttc cttttcaacc tgaacaacga gtatgttctt gacgcataca   2580
gaatgggtga caagctgaaa tttgccaacc atgcccctga cccgaattgc tatgccaagg   2640
ttatcatggt aactggtgat catagagtgg gcatattcgc caaagaaaga atcctcgctg   2700
gtgaagagtt attctacgat taccgctatg agcctgacag agcccctgct gggcccgta    2760
agcctgaggc gtcgggagca aaggatgatg ggcaaccgtt caatgggcgt gcaaagaagc   2820
tcgcccaaaa aacagaggc tgaatctgat ttgattcttt cattgttagg acaaatttgg    2880
cagccattca actaatataa ggaacctgtc attcataggc cccaatttat ttgaactcgt   2940
cattgtaact cgtatgtgct tgaattctcc atggcagctg gtcctgccat ccgtagagtt   3000
aggtcccgtt tgttttgagg aactaaaaat taatccctct attttagtca cattgagtct   3060
tagattgtta acggcggga ctaaaacaaa agactaaact attgtctct agtacctcaa     3120
gccatgacta aagggaata aatcatataa attttatttt tatccttcct ttaaaaaaaa    3180
```

<210> SEQ ID NO 2
<211> LENGTH: 931
<212> TYPE: PRT
<213> ORGANISM: Zea mays

<400> SEQUENCE: 2

```
Met Glu Ala Glu Ala Ala Ala Val Val Ala Ser Ser Ala Ser Ala
  1               5                  10                  15

Ser Ala Ser Ala Gly Arg Ser Arg Pro Ser Ser Ala Ala Ser Val
                 20                  25                  30

Thr Ser Asn Ser Ala Val Arg Ala Gly Glu Glu Asn Ala Ala Ser Leu
                 35                  40                  45

Tyr Val Leu Ser Val Ile Asp Ser Leu Lys Lys Arg Ile Thr Ala Asp
     50                  55                  60

Arg Leu Thr Tyr Ile Lys Asn Arg Ile Gly Glu Asn Lys Thr Asn Ile
 65                  70                  75                  80

Ser Ser Tyr Thr Gln Arg Thr Tyr Asn Leu Ser Lys Asn Arg Gln Ile
                 85                  90                  95

Ser Thr Ser Lys Gly Thr Asp Ser Ala Ser Asn Leu Leu Thr Lys Arg
                100                 105                 110

Gln Asp Asp Ala Leu Cys Thr Leu His Ser Leu Asp Ile Ile Pro Val
            115                 120                 125

Asp Lys Asp Gly Gly Thr Phe Gln Asp Glu Ser Pro Phe Ser Ser Ser
    130                 135                 140

Asn Val Met Phe Gly Gly Asn Leu Gly Pro Lys Asn Ala Ile Ile Arg
145                 150                 155                 160

Pro Ile Lys Leu Pro Glu Val Pro Lys Leu Pro Pro Tyr Thr Thr Trp
                165                 170                 175

Ile Phe Leu Asp Arg Asn Gln Arg Met Thr Glu Asp Gln Ser Val Leu
            180                 185                 190

Gly Arg Arg Arg Ile Tyr Tyr Asp Thr Ser Cys Gly Glu Ala Leu Ile
        195                 200                 205

Cys Ser Asp Ser Glu Asp Glu Ala Ile Glu Asp Glu Glu Glu Lys Lys
    210                 215                 220
```

```
Glu Phe Lys His Ser Glu Asp His Ile Ile Arg Met Thr Val Gln Glu
225                 230                 235                 240

Cys Gly Met Ser Asp Ala Val Leu Gln Thr Leu Ala Arg His Met Glu
            245                 250                 255

Arg Ala Ala Asp Asp Ile Lys Ala Arg Tyr Glu Ile Leu His Gly Glu
                260                 265                 270

Lys Thr Lys Asp Ser Cys Lys Lys Gly Thr Glu His Asn Val Lys Val
            275                 280                 285

Glu Asp Leu Tyr Cys Asp Lys Asp Leu Asp Ala Ala Leu Asp Ser Phe
        290                 295                 300

Asp Asn Leu Phe Cys Arg Arg Cys Leu Val Phe Asp Cys Lys Leu His
305                 310                 315                 320

Gly Cys Ser Gln Asp Leu Val Phe Pro Pro Glu Lys Gln Pro Ala Trp
                325                 330                 335

Arg Gly Val Asp Asp Ser Val Pro Cys Gly Ile His Ser His Lys Leu
            340                 345                 350

Ala Ser Glu Pro Asp Ser Ala Ala Gly Ala Asp Pro Met Leu Phe Asp
            355                 360                 365

Val Glu Glu Pro Thr His Ser Ser Asp Asn Val Met Asn Gln Pro Gly
        370                 375                 380

Ser Asn Arg Lys Lys Asn Gly Ser Ser Gly Arg Lys Thr Lys Ser Gln
385                 390                 395                 400

Gln Ser Glu Ser Ser Thr Ala Arg Val Ile Ser Glu Ser Ser Ala
                405                 410                 415

Ser Glu Val His Pro Ile Ser Asn Lys Ser Pro Gln His Ser Pro Ser
            420                 425                 430

Pro Ser Lys Val Lys Ile Gly Pro Lys Gly Ile Arg Lys Ile Thr
            435                 440                 445

Asn Arg Arg Ile Ala Glu Arg Ile Leu Met Ser Val Lys Lys Gly Gln
450                 455                 460

Arg Glu Met Ala Ser Ser Asp Ser Asn Phe Val Ser Gly Tyr Leu Leu
465                 470                 475                 480

Ala Arg Asp Met Lys Leu Arg Ser Asp Thr Arg Asn Gly Asn Lys Glu
            485                 490                 495

Leu Ile Val Ser Ser Gln Gln Ser Ser Pro Ser Thr Arg Ser Ser Lys
            500                 505                 510

Lys Lys Ser Thr Pro Gln Ile Gly Asn Ser Ser Ala Phe Ala Glu Ala
            515                 520                 525

His Asn Asp Ser Thr Glu Glu Ala Asn Asn Arg His Ser Ala Thr Asp
530                 535                 540

Gly Tyr Asp Ser Ser Arg Lys Glu Glu Phe Val Asn Glu Asn Leu Cys
545                 550                 555                 560

Lys Gln Glu Val Tyr Leu Arg Ser Trp Lys Ala Ile Glu Gln Gly Leu
            565                 570                 575

Leu Val Lys Gly Leu Glu Ile Phe Gly Arg Asn Ser Cys Leu Ile Ala
            580                 585                 590

Arg Asn Leu Leu Gly Gly Met Lys Thr Cys Lys Asp Val Phe Gln Tyr
            595                 600                 605

Met Asn Tyr Ile Glu Asn Asn Ser Ala Ser Gly Ala Leu Ser Gly Val
        610                 615                 620

Asp Ser Leu Val Lys Gly Tyr Ile Lys Gly Thr Glu Leu Arg Thr Arg
625                 630                 635                 640
```

Ser Arg Tyr Phe Arg Arg Arg Gly Lys Val Arg Arg Leu Lys Tyr Thr
            645                 650                 655

Trp Lys Ser Ala Gly Tyr Asn Phe Lys Arg Ile Thr Glu Arg Lys Asp
            660                 665                 670

Gln Pro Cys Arg Gln Tyr Asn Pro Cys Gly Cys Gln Ser Thr Cys Gly
            675                 680                 685

Lys Gln Cys Pro Cys Leu Ser Asn Gly Thr Cys Cys Glu Lys Tyr Cys
            690                 695                 700

Gly Cys Pro Lys Ile Cys Lys Asn Arg Phe Arg Gly Cys His Leu Cys
705                 710                 715                 720

Lys Ser Gln Cys Arg Ser Arg Gln Cys Pro Cys Phe Ala Ala Asp Arg
            725                 730                 735

Glu Cys Asp Pro Asp Val Cys Arg Asn Cys Trp Val Gly Cys Gly Asp
            740                 745                 750

Gly Thr Leu Gly Val Pro Asn Gln Arg Gly Asp Asn Tyr Glu Cys Arg
            755                 760                 765

Asn Met Lys Leu Leu Leu Lys Gln Gln Gln Arg Val Leu Leu Gly Arg
            770                 775                 780

Ser Asp Val Ser Gly Trp Gly Ala Phe Leu Lys Asn Ser Val Ser Lys
785                 790                 795                 800

His Glu Tyr Leu Gly Glu Tyr Thr Gly Glu Leu Ile Ser His Lys Glu
            805                 810                 815

Ala Asp Lys Arg Gly Lys Ile Tyr Asp Arg Glu Asn Ser Ser Phe Leu
            820                 825                 830

Phe Asn Leu Asn Asn Glu Tyr Val Leu Asp Ala Tyr Arg Met Gly Asp
            835                 840                 845

Lys Leu Lys Phe Ala Asn His Ala Pro Asp Pro Asn Cys Tyr Ala Lys
            850                 855                 860

Val Ile Met Val Thr Gly Asp His Arg Val Gly Ile Phe Ala Lys Glu
865                 870                 875                 880

Arg Ile Leu Ala Gly Glu Glu Leu Phe Tyr Asp Tyr Arg Tyr Glu Pro
            885                 890                 895

Asp Arg Ala Pro Ala Trp Ala Arg Lys Pro Glu Ala Ser Gly Ala Lys
            900                 905                 910

Asp Asp Gly Gln Pro Phe Asn Gly Arg Ala Lys Lys Leu Ala Gln Asn
            915                 920                 925

Asn Arg Gly
    930

<210> SEQ ID NO 3
<211> LENGTH: 3030
<212> TYPE: DNA
<213> ORGANISM: Zea mays

<400> SEQUENCE: 3
ccgtcgcaga attcgcgcca ccgcccgcga tggcttcgtc ctcgaaggcc tccgattcct      60
cccaacgatc caagcggtcg gatcagggga tgggcaagga cgccgctgcc gcctctgttg     120
tcccgatcca cgcgaacctg acgcagctga tacggcaagt ccaatcgggg cgcctcgcgt     180
acatcaagga gaaattggag gtgaacagga aaacgctgca gaggcactcc tgctcgctgt     240
tcgacgtggc agcggcggcg gaggtggcgt cgagggcac cgatggcggc aacgcgctgt     300
cacagcgcgc ggcggagaga cagtgtgggt cagacctggc aaacgggata ggggagaggg     360
atgtggtttc cgttcacgag gagaacctgg ctaccggtac gctcgcgctc tccagctcgg     420

-continued

```
gcgctaccgc gcagcggaca attgtgcggt tcgtgaagct gccgctggtt gagaagatcc    480
ctccgtacac cacttggatc ttcctggaca aaaaccaaag aatggctgac gatcagtcag    540
ttgttggtag gagaaggata tactatgata cagttggaaa cgaggctctg atctgcagtg    600
acagtgatga agaaattcca gaaccagagg aagagaaaca cttttcaca aagggagaag     660 atcatttgat atggagagct actcaagacc atgggttaaa ccaagaggtt gttaatgtcc    720
tttgccagtt tattggtgca accccatcag aaattgagga agatctgaa gtcctatttg    780 agaaaaatga gaagcactca ggatcttcag ataagataga gagccgactt tctcttgaca   840
aaactatgga tgccgttctg gattcttttg ataatctctt ctgccgcaga tgcttggttt    900
ttgattgccg ccttcatggt tgttcacaga atttggtatt tccatgtgag aagcaaccct    960
acagctttga ccctgatgaa aacaagaagc catgtggtca tttgtgctac cttcgatttc   1020
cccagtggag agaaggattt aaagagatgc atgatgatgg tcttgctggt ggtgcaacat    1080
atactatgga atcgggaact gcctcacaga gagttgatgt taatgttatg tatgaatcag    1140
aagattcaaa ccgacagaaa ggcaacatta ggtccatgac actagttgga accagtggac    1200
caaaaataat ttcttctgtc agtgcggaag aaagcactac tactccagca gatatctctg    1260
aaacagagaa tgtatcctct gatttgcctc ccagtagttt aaggaaacac aagatttcaa    1320 acatggacc taggtacagg gagcattctc ctggcaaaag gcagaaggtt ttcacttctg    1380
acatttcttt tgaaggcagt ataatgaata aactttccat tccggagatt cgtgacacaa    1440
gactagagtc cagagaatct ggtggtgata aactacgaat tcttgacgag tccactaaga    1500
agacttcaag gaaagatatg tgtggggaaa gcccagctac taccatggaa aatgtgggaa    1560
gacagagtaa taaagtgtat tcaacaaaga atttcttgga gtccactctt tcttgttgga    1620
gtgccttaga gcgagatcta tacttgaagg gcatagagat atttggaaag aacagctgtc    1680
tcatcgccag aaacttacta tctggtctta agacctgcat agaagtggca aactacatgt    1740
ataacaatgg tgcagcgatg gcgaagagac ctctcttgaa taaatccatc tcaggcgact    1800
ttgcagaaaa tgaacaagac tacatggagc aagacatggc tgccagaaca agaatctatc    1860
gtcggagggg ccgcaatcga aagctgaaat atacttggaa atctgcaggg catccaactg    1920
ttagaaaaag aactgatgac gggaagcaat gttacacaca atatagccca tgtgcgtgcc    1980
agcaaatgtg tggtaaagat tgcccctgtg cggacaaggg aacttgctgt gagaagtact    2040
gtgggtgttc gaagagctgc aaaaacaagt ttagaggctg tcattgtgca aaaagccaat    2100
gcagaagcag acagtgcccc tgttttgcag ccagtcgtga atgtgatcca gatgtttgta    2160
ggaattgctg ggtgagctgt ggagatggtt cactaggtga gccacttgca agaggtgatg    2220
gttatcagtg tggaaatatg aagctccttt tgaaacaaca gcaaaggatt ttgttaggaa    2280
gatctgatgt tgcaggttgg ggtgcattca ttaagaatcc tgtaaataaa aatgattatc    2340
ttggagaata tactggtgaa ttgatctctc acaggaagc agacaaacgc ggcaaaattt     2400
atgaccgggc aaactcatct tttctgttcg atttaaatga ccagtatgtg ttggatgctt    2460
atcgcaaggg ggacaaattg aagttcgcaa atcactcatc taaccccaac tgctatgcaa    2520
aggtgatgct ggtggctggc gaccatcggg ttggtatata tgcgaaggag catattgagg    2580
ctagcgagga actctttat gattatcgtt atggacctga ccaggctccg gcttgggcta    2640
ggagacccga aggatcaaag aaggacgagg catccttctc tcaccgtcga gcacacaaag    2700
tggctcgata gctgaagagt cgctccggat gatacaatat gcagtaaact taatacttaa    2760
tacatgattc agtcctagtt cattggtaga taaacatgct atatactatc cattagtaaa    2820
```

-continued

```
taaactctca ttcatcgagt tggagaataa atgcgtataa acatatgtgg acctcaggtc    2880
gggaaggtgg caaccttgtt agtttgagca ccaacaggtt ctcaaacttg agtggctatt    2940
gctagagtat caaataatgg ctgcgactat agccttgttt gtatattttc ttggtgagat    3000
gaaataattt gtcaaatgta cacttaaaaa                                    3030
```

```
<210> SEQ ID NO 4
<211> LENGTH: 893
<212> TYPE: PRT
<213> ORGANISM: Zea mays

<400> SEQUENCE: 4
```

Met Ala Ser Ser Lys Ala Ser Asp Ser Ser Gln Arg Ser Lys Arg
 1               5                  10                  15

Ser Asp Gln Gly Met Gly Lys Asp Ala Ala Ala Ser Val Val Pro
            20                  25                  30

Ile His Ala Asn Leu Thr Gln Leu Ile Arg Gln Val Gln Ser Gly Arg
        35                  40                  45

Leu Ala Tyr Ile Lys Glu Lys Leu Glu Val Asn Arg Lys Thr Leu Gln
    50                  55                  60

Arg His Ser Cys Ser Leu Phe Asp Val Ala Ala Ala Glu Val Ala
65                  70                  75                  80

Ser Arg Gly Thr Asp Gly Gly Asn Ala Leu Ser Gln Arg Ala Ala Glu
                85                  90                  95

Arg Gln Cys Gly Ser Asp Leu Ala Asn Gly Ile Gly Glu Arg Asp Val
            100                 105                 110

Val Ser Val His Glu Glu Asn Leu Ala Thr Gly Thr Leu Ala Leu Ser
        115                 120                 125

Ser Ser Gly Ala Thr Ala Gln Arg Thr Ile Val Arg Phe Val Lys Leu
    130                 135                 140

Pro Leu Val Glu Lys Ile Pro Pro Tyr Thr Thr Trp Ile Phe Leu Asp
145                 150                 155                 160

Lys Asn Gln Arg Met Ala Asp Asp Gln Ser Val Val Gly Arg Arg
                165                 170                 175

Ile Tyr Tyr Asp Thr Val Gly Asn Glu Ala Leu Ile Cys Ser Asp Ser
            180                 185                 190

Asp Glu Glu Ile Pro Glu Pro Glu Glu Lys His Phe Phe Thr Lys
        195                 200                 205

Gly Glu Asp His Leu Ile Trp Arg Ala Thr Gln Asp His Gly Leu Asn
    210                 215                 220

Gln Glu Val Val Asn Val Leu Cys Gln Phe Ile Gly Ala Thr Pro Ser
225                 230                 235                 240

Glu Ile Glu Glu Arg Ser Glu Val Leu Phe Glu Lys Asn Glu Lys His
                245                 250                 255

Ser Gly Ser Ser Asp Lys Ile Glu Ser Arg Leu Ser Leu Asp Lys Thr
            260                 265                 270

Met Asp Ala Val Leu Asp Ser Phe Asp Asn Leu Phe Cys Arg Arg Cys
        275                 280                 285

Leu Val Phe Asp Cys Arg Leu His Gly Cys Ser Gln Asn Leu Val Phe
    290                 295                 300

Pro Cys Glu Lys Gln Pro Tyr Ser Phe Asp Pro Asp Glu Asn Lys Lys
305                 310                 315                 320

Pro Cys Gly His Leu Cys Tyr Leu Arg Phe Pro Gln Trp Arg Glu Gly
                325                 330                 335

```
Phe Lys Glu Met His Asp Asp Gly Leu Ala Gly Gly Ala Thr Tyr Thr
            340                 345                 350

Met Glu Ser Gly Thr Ala Ser Gln Arg Val Asp Val Asn Val Met Tyr
            355                 360                 365

Glu Ser Glu Asp Ser Asn Arg Gln Lys Gly Asn Ile Arg Ser Met Thr
            370                 375                 380

Leu Val Gly Thr Ser Gly Pro Lys Ile Ile Ser Ser Val Ser Ala Glu
385                 390                 395                 400

Glu Ser Thr Thr Thr Pro Ala Asp Ile Ser Glu Thr Glu Asn Val Ser
            405                 410                 415

Ser Asp Leu Pro Pro Ser Ser Leu Arg Lys His Lys Ile Ser Lys His
            420                 425                 430

Gly Pro Arg Tyr Arg Glu His Ser Pro Gly Lys Arg Gln Lys Val Phe
            435                 440                 445

Thr Ser Asp Ile Ser Phe Glu Gly Ser Ile Met Asn Lys Leu Ser Ile
            450                 455                 460

Pro Glu Ile Arg Asp Thr Arg Leu Glu Ser Arg Glu Ser Gly Gly Asp
465                 470                 475                 480

Lys Leu Arg Ile Leu Asp Glu Ser Thr Lys Thr Ser Arg Lys Asp
            485                 490                 495

Met Cys Gly Glu Ser Pro Ala Thr Thr Met Glu Asn Val Gly Arg Gln
            500                 505                 510

Ser Asn Lys Val Tyr Ser Thr Lys Asn Phe Leu Glu Ser Thr Leu Ser
            515                 520                 525

Cys Trp Ser Ala Leu Glu Arg Asp Leu Tyr Leu Lys Gly Ile Glu Ile
            530                 535                 540

Phe Gly Lys Asn Ser Cys Leu Ile Ala Arg Asn Leu Leu Ser Gly Leu
545                 550                 555                 560

Lys Thr Cys Ile Glu Val Ala Asn Tyr Met Tyr Asn Asn Gly Ala Ala
            565                 570                 575

Met Ala Lys Arg Pro Leu Leu Asn Lys Ser Ile Ser Gly Asp Phe Ala
            580                 585                 590

Glu Asn Glu Gln Asp Tyr Met Glu Gln Asp Met Ala Ala Arg Thr Arg
            595                 600                 605

Ile Tyr Arg Arg Arg Gly Arg Asn Arg Lys Leu Lys Tyr Thr Trp Lys
            610                 615                 620

Ser Ala Gly His Pro Thr Val Arg Lys Arg Thr Asp Asp Gly Lys Gln
625                 630                 635                 640

Cys Tyr Thr Gln Tyr Ser Pro Cys Ala Cys Gln Gln Met Cys Gly Lys
            645                 650                 655

Asp Cys Pro Cys Ala Asp Lys Gly Thr Cys Cys Glu Lys Tyr Cys Gly
            660                 665                 670

Cys Ser Lys Ser Cys Lys Asn Lys Phe Arg Gly Cys His Cys Ala Lys
            675                 680                 685

Ser Gln Cys Arg Ser Arg Gln Cys Pro Cys Phe Ala Ala Ser Arg Glu
            690                 695                 700

Cys Asp Pro Asp Val Cys Arg Asn Cys Trp Val Ser Cys Gly Asp Gly
705                 710                 715                 720

Ser Leu Gly Glu Pro Leu Ala Arg Gly Asp Gly Tyr Gln Cys Gly Asn
            725                 730                 735

Met Lys Leu Leu Leu Lys Gln Gln Gln Arg Ile Leu Leu Gly Arg Ser
            740                 745                 750
```

-continued

```
Asp Val Ala Gly Trp Gly Ala Phe Ile Lys Asn Pro Val Asn Lys Asn
        755                 760                 765

Asp Tyr Leu Gly Glu Tyr Thr Gly Glu Leu Ile Ser His Lys Glu Ala
        770                 775                 780

Asp Lys Arg Gly Lys Ile Tyr Asp Arg Ala Asn Ser Ser Phe Leu Phe
785                 790                 795                 800

Asp Leu Asn Asp Gln Tyr Val Leu Asp Ala Tyr Arg Lys Gly Asp Lys
                805                 810                 815

Leu Lys Phe Ala Asn His Ser Ser Asn Pro Asn Cys Tyr Ala Lys Val
            820                 825                 830

Met Leu Val Ala Gly Asp His Arg Val Gly Ile Tyr Ala Lys Glu His
                835                 840                 845

Ile Glu Ala Ser Glu Glu Leu Phe Tyr Asp Tyr Arg Tyr Gly Pro Asp
        850                 855                 860

Gln Ala Pro Ala Trp Ala Arg Arg Pro Glu Gly Ser Lys Lys Asp Glu
865                 870                 875                 880

Ala Ser Phe Ser His Arg Arg Ala His Lys Val Ala Arg
                885                 890
```

<210> SEQ ID NO 5
<211> LENGTH: 340
<212> TYPE: PRT
<213> ORGANISM: Zea mays

<400> SEQUENCE: 5

```
Met Ala Ser Ser Lys Ala Ser Asp Ser Ser Gln Arg Ser Lys Arg
 1               5                  10                  15

Ser Asp Gln Gly Met Gly Lys Asp Ala Ala Ala Ser Val Val Pro
                20                  25                  30

Ile His Ala Asn Leu Thr Gln Leu Ile Arg Gln Val Gln Ser Gly Arg
            35                  40                  45

Leu Ala Tyr Ile Lys Glu Lys Leu Glu Val Asn Arg Lys Thr Leu Gln
     50                  55                  60

Arg His Ser Cys Ser Leu Phe Asp Val Ala Ala Ala Glu Val Ala
 65                  70                  75                  80

Ser Arg Gly Thr Asp Gly Gly Asn Ala Leu Ser Gln Arg Ala Ala Glu
                85                  90                  95

Arg Gln Cys Gly Ser Asp Leu Ala Asn Gly Ile Gly Glu Arg Asp Val
            100                 105                 110

Val Ser Val His Glu Glu Asn Leu Ala Thr Gly Thr Leu Ala Leu Ser
        115                 120                 125

Ser Ser Gly Ala Thr Ala Gln Arg Thr Ile Val Pro Val Arg Glu Ala
    130                 135                 140

Ala Leu Val Glu Lys Ile Pro Pro Tyr Thr Thr Trp Ile Phe Leu Asp
145                 150                 155                 160

Lys Asn Gln Arg Met Ala Asp Asp Gln Ser Val Val Gly Arg Arg
                165                 170                 175

Ile Tyr Tyr Asp Thr Val Gly Asn Glu Ala Leu Ile Cys Ser Asp Ser
            180                 185                 190

Asp Glu Glu Ile Pro Glu Pro Glu Glu Lys His Phe Phe Thr Lys
        195                 200                 205

Gly Glu Asp His Leu Ile Trp Arg Ala Thr Gln Asp His Gly Leu Asn
    210                 215                 220

Gln Glu Val Val Asn Val Leu Cys Gln Phe Ile Gly Ala Thr Pro Ser
225                 230                 235                 240
```

```
Glu Ile Glu Glu Arg Ser Glu Val Leu Phe Glu Lys Asn Glu Lys His
                245                 250                 255

Ser Gly Ser Ser Asp Lys Ile Glu Ser Arg Leu Ser Leu Asp Lys Thr
            260                 265                 270

Met Asp Ala Val Leu Asp Ser Phe Asp Asn Leu Phe Cys Arg Arg Cys
        275                 280                 285

Leu Val Phe Asp Cys Arg Leu His Gly Cys Ser Gln Asn Leu Val Phe
    290                 295                 300

Pro Cys Glu Lys Gln Pro Tyr Ser Phe Asp Pro Asp Glu Asn Lys Lys
305                 310                 315                 320

Pro Cys Gly His Leu Cys Tyr Leu Arg Leu Ser His Arg Gln Lys Leu
                325                 330                 335

Thr Ile Trp Ser
            340

<210> SEQ ID NO 6
<211> LENGTH: 340
<212> TYPE: PRT
<213> ORGANISM: Zea mays

<400> SEQUENCE: 6

Met Ala Ser Ser Lys Ala Ser Asp Ser Ser Gln Arg Ser Lys Arg
1               5                   10                  15

Ser Asp Gln Gly Met Gly Lys Asp Ala Ala Ala Ser Val Val Pro
                20                  25                  30

Ile His Ala Asn Leu Thr Gln Leu Ile Arg Gln Val Gln Ser Gly Arg
                35                  40                  45

Leu Ala Tyr Ile Lys Glu Lys Leu Glu Val Asn Arg Lys Thr Leu Gln
    50                  55                  60

Arg His Ser Cys Ser Leu Phe Asp Val Ala Ala Ala Glu Val Ala
65                  70                  75                  80

Ser Arg Gly Thr Asp Gly Gly Asn Ala Leu Ser Gln Arg Ala Ala Glu
                85                  90                  95

Arg Gln Cys Gly Ser Asp Leu Ala Asn Gly Ile Gly Glu Arg Asp Val
            100                 105                 110

Val Ser Val His Glu Glu Asn Leu Ala Thr Gly Thr Leu Ala Leu Ser
                115                 120                 125

Ser Ser Gly Ala Thr Ala Gln Arg Thr Ile Val Pro Val Arg Glu Ala
            130                 135                 140

Ala Leu Val Glu Lys Ile Pro Pro Tyr Thr Thr Trp Ile Phe Leu Asp
145                 150                 155                 160

Lys Asn Gln Arg Met Ala Asp Asp Gln Ser Val Val Gly Arg Arg
                165                 170                 175

Ile Tyr Tyr Asp Thr Val Gly Asn Glu Ala Leu Ile Cys Ser Asp Ser
            180                 185                 190

Asp Glu Glu Ile Pro Glu Pro Glu Glu Lys His Phe Phe Thr Lys
            195                 200                 205

Gly Glu Asp His Leu Ile Trp Arg Ala Thr Gln Asp His Gly Leu Asn
    210                 215                 220

Gln Glu Val Val Asn Val Leu Cys Gln Phe Ile Gly Ala Thr Pro Ser
225                 230                 235                 240

Glu Ile Glu Glu Arg Ser Glu Val Leu Phe Glu Lys Asn Glu Lys His
                245                 250                 255

Ser Gly Ser Ser Asp Lys Ile Glu Ser Arg Leu Ser Leu Asp Lys Thr
            260                 265                 270
```

```
Met Asp Ala Val Leu Asp Ser Phe Asp Asn Leu Phe Cys Arg Arg Cys
        275                 280                 285

Leu Val Phe Asp Cys Arg Leu His Gly Cys Ser Gln Asn Leu Val Phe
        290                 295                 300

Pro Cys Glu Lys Gln Pro Tyr Ser Phe Asp Pro Asp Glu Asn Lys Lys
305                 310                 315                 320

Pro Cys Gly His Leu Cys Tyr Leu Arg Leu Ser His Arg Gln Lys Leu
                325                 330                 335

Thr Ile Trp Ser
            340

<210> SEQ ID NO 7
<211> LENGTH: 22
<212> TYPE: DNA
<213> ORGANISM: Zea mays

<400> SEQUENCE: 7
gggtgtggtg atggtacatt gg                                              22

<210> SEQ ID NO 8
<211> LENGTH: 25
<212> TYPE: DNA
<213> ORGANISM: Zea mays

<400> SEQUENCE: 8
cagcttgtca cccattctgt atgcg                                           25

<210> SEQ ID NO 9
<211> LENGTH: 25
<212> TYPE: DNA
<213> ORGANISM: Zea mays

<400> SEQUENCE: 9
tgcctcgtcc ttctttgatc cttcg                                           25

<210> SEQ ID NO 10
<211> LENGTH: 25
<212> TYPE: DNA
<213> ORGANISM: Zea mays

<400> SEQUENCE: 10
ctcacaagga agcagacaaa cgcgg                                           25

<210> SEQ ID NO 11
<211> LENGTH: 25
<212> TYPE: DNA
<213> ORGANISM: Zea mays

<400> SEQUENCE: 11
taccttggtg agtacactgg ggaac                                           25

<210> SEQ ID NO 12
<211> LENGTH: 24
<212> TYPE: DNA
<213> ORGANISM: Zea mays

<400> SEQUENCE: 12
ccatttcgtg tatcagacct aagc                                            24
```

```
<210> SEQ ID NO 13
<211> LENGTH: 18
<212> TYPE: DNA
<213> ORGANISM: Zea mays

<400> SEQUENCE: 13
catcaacgcc ctccaagc                                                 18

<210> SEQ ID NO 14
<211> LENGTH: 25
<212> TYPE: DNA
<213> ORGANISM: Zea mays

<400> SEQUENCE: 14
tgccacattc ttgaactgtc atccg                                         25

<210> SEQ ID NO 15
<211> LENGTH: 23
<212> TYPE: DNA
<213> ORGANISM: Zea mays

<400> SEQUENCE: 15
gcacagtgac atcctcgaaa acg                                           23

<210> SEQ ID NO 16
<211> LENGTH: 17
<212> TYPE: DNA
<213> ORGANISM: Zea mays

<400> SEQUENCE: 16
gtccctgctc aattgcc                                                  17

<210> SEQ ID NO 17
<211> LENGTH: 20
<212> TYPE: DNA
<213> ORGANISM: Zea mays

<400> SEQUENCE: 17
gcggacaatt gtgcggttcg                                               20

<210> SEQ ID NO 18
<211> LENGTH: 19
<212> TYPE: DNA
<213> ORGANISM: Zea mays

<400> SEQUENCE: 18
ggttgttcac agaatttgg                                                19

<210> SEQ ID NO 19
<211> LENGTH: 26
<212> TYPE: DNA
<213> ORGANISM: Zea mays

<400> SEQUENCE: 19
cttcctaaca aaatcctttg ctgttg                                        26

<210> SEQ ID NO 20
<211> LENGTH: 18
<212> TYPE: DNA
<213> ORGANISM: Zea mays

<400> SEQUENCE: 20
ttgctccatg tagtcttg                                                 18
```

POLYCOMB GENES FROM MAIZE—*MEZ1* AND *MEZ2*

RELATED APPLICATION INFORMATION

This application is a continuation of U.S. application Ser. No. 11/633,204, filed on Dec. 4, 2006, abandoned, which is a continuation of U.S. application Ser. No. 11/230,145, filed on Sep. 19, 2005, abandoned, which is a continuation of U.S. application Ser. No. 09/906,453, filed on Jul. 16, 2001, abandoned, which claims priority to U.S. Application No. 60/218,745, filed on Jul. 17, 2000, the contents of which are herein incorporated by reference.

TECHNICAL FIELD OF THE INVENTION

The present invention relates to plant genetic engineering. More specifically, the present invention relates to polycomb nucleic acids cloned from *Zea mays L.*

BACKGROUND OF THE INVENTION

In eukaryotes, gene expression patterns are regulated in response to developmental and environmental cues. These changes in gene expression patterns are often the result of specific transcriptional regulators. In many cases, this change in gene expression must be stably maintained through many mitotic cell divisions even though the transcriptional regulator that effected the change in expression is only present transiently. The stable maintenance of a transcription state is performed by a set of nonspecific factors. These factors are important in regulating chromatin states and establishing a chromatin "memory" to effectively maintain the proper gene expression patterns. In *Drosophila*, the Polycomb group, PcG, genes are involved in nonspecific, long-term stabilization of transcriptional repression. Recently, homologs of some of the polycomb group genes have been shown to affect developmental gene regulation in other species.

There are at least thirteen PcG proteins in *Drosophila*. Mutations in any of the thirteen identified PcG genes can lead to lethality during early development (See, Simon, J., *Current Opinion in Cell Biology*, 7(3):376-85 (1995); Pirrotta, V., *Curr. Opin. Gen. Dev.*, 7(2):249-58 (1997); Pirrotta, V., *Cell*, 93(3):333-6 (1998)). The cause of this lethality is the failure to maintain transcriptional repression of homeotic genes of the *Antennopedia/bithorax* complex. The expression pattern of these homeotic genes is controlled in the embryo by activators and repressors that define body segments. During gastrulation, these specific factors are no longer present and PcG protein complexes stabilize a silenced state at genes repressed by the specific factors. Importantly, PcG complexes silence different targets in different cell lineages. This indicates that PcG complexes are able to silence based on factors such as transcription state and not just on sequence. An antagonistic set of factors which maintain the active transcriptional state, the trithorax group, also exist in *Drosophila*.

In addition to playing a role in developmentally regulated repression of gene expression, the PcG proteins are also involved in maintaining a silenced state at other loci. When high copy numbers (>3) of a white-Adh transgene are introduced into the *Drosophila* genome the level of white-Adh expression becomes reduced via cosuppression (Pal-Bhadra et al., *Cell*, 90:479-490 (1997)). In addition to reductions in the expression of the transgenes, the expression of the endogenous Adh gene is reduced as well. This cosuppression is relieved by mutations in polycomb (Pc) or polycomblike (pcl). The cosuppression is based on a homology sensing mechanism that leads to repression via PcG proteins (Pal-Bhadra et al., *Cell*, 99:35-46 (1999)). The PcG protein, enhancer of zeste, E(z), is required for trans-silencing of P-elements (Roche et al., *Genetics*, 149(4):1839-55 (1998)). Increased expression of E(z) or the human homolog (EZH2) results in enhancing position effect variegation (PEV) of a heterochromatin associated white locus (Laible et al., *EMBO J.*, 16(11) 3219-32 (1997)). The EZH2 gene was also able to restore telomere mediated gene repression in *S. cerevisiae* (Laible et al., *EMBO J.*, 16(11) 3219-32 (1997)). These studies suggest that the PcG proteins can play a role in epigenetic inactivation of gene expression distinct from the role of developmental regulation.

Many of the domains present in the PcG proteins that have been cloned are implicated in protein-protein interactions. The esc and E(z) proteins have been shown to interact with each other in a yeast two hybrid system and through in vitro binding assays (Jones et al., *Cell Biol.*, 18(5):2825-34 (1998)). Homotypic and heterotypic interactions based on the SPM domain have been documented for Sex combs on midleg (Scm) and ph (Bornemann et al., *Development*, 122(5):1621-30 (1996); Peterson et al., *Mol. Cell Biol.*, 17(11):6683-92 (1997)). The *Xenopus* Pc homolog, Xpc, forms complexes with itself and Bmi-1 (a psc homolog) (Reijnen et al., *Mech. Dev.*, 53(1):35-46 (1995)). In other yeast two-hybrid screens, ph interacts with itself and with Psc, and Psc interacts with Pc (Pirotta, V., *Curr. Opin. Gen. Dev.*, 7(2):249-58 (1997)). These results indicate the presence of a large complex formed by PcG proteins that is formed based on multiple protein-protein interactions among various PcG members.

Recent evidence suggests that PcG proteins actually form two distinct complexes. One complex contains E(z) and esc which have been found to directly interact (van Lohuizen et al., *Mol. Cell Biol.*, 18(6):3572-9 (1998); Jones et al., *Mol. Cell Biol.*, 18(5):2825-34 (1998), Sewalt et al., *Mol. Cell Biol.*, 18(6):3586-95 (1998); Ng et al., *Mol. Cell Biol.*, 20(9):3069-78 (2000)). The second complex is the PRC1 complex (which includes Pc/Ph/Scm/Psc).

Homologs from PcG proteins have been characterized in a number of species. Vertebrates appear to contain the most homologs of PcG proteins (Simon, *Current Opinion in Cell Biology*, 7(3):376-85 (1995)). Homologs of psc, Pc, ph, E(z) and esc have been cloned in mammals. The role of PcG proteins in mammals is believed to be very similar to the role in *Drosophila*.

While many of the domains present in PcG proteins are found in yeast proteins, no PcG homologs are present in the *S. cerevisiae* genome. In *C. elegans* and *Arabidopsis*, homologs of two PcG proteins, E(z) and esc are found. A SET domain and a cys-rich region are found in E(z) (Carrington et al., *Development*, 122(12):4073-83 (1996); Jones et al., *Genetics*, 126(1):185-99 (1990); Jones, R S, et al., *Mol. Cell. Biol.*, 13(10):6357-66 (1993)). The esc proteins contain a series of seven WD-40 repeats (Gutjahr et al., *EMBO J.*, 14(17):4296-306 (1995); Simon et al., *Mech. Devt.*, 53(2):197-208 (1995)).

The E(z) and esc homologs (maternal effect sterile-2 (mes-2) and maternal effect sterile-6 (mes-6)) from *C. elegans* were identified in a screen for maternal-effect mutations that result in sterile offspring (Holdeman et al., *Development*, 125(13):2457-67 (1998), Korf et al., *Development*, 125(13):2469-78 (1998)). The mes-2 and mes-6 genes are implicated as maternal genes required for germline immortality. Both mes-2 and mes-6 are localized to the nucleus of all embryonic cells and the nuclei of germline cells in larvae and adults. This localization is dependent upon each other and another protein, mes-3 (Holdeman et al., *Development*, 125(13):2457-67

(1998), Korf et al., *Development*, 125(13):2469-78 (1998)). Transgene arrays in the *C. elegans* genome are frequently silenced in germline cells (Kelly et al., *Development*, 125 (13):2451-6 (1998)). Mutations in mes-2 and mes-6 completely alleviate silencing of transgenes in the germline cells (Kelly et al., *Development*, 125(13):2451-6 (1998). These results suggest that the PcG proteins of *C. elegans*, mes-2 and mes-6 are involved in transcriptional repression specifically in the germline cells. It is likely that mes-2 and mes-6 repress transcription of genes that would lead to a differentiated state.

*Arabidopsis* also contains homologs of E(z) and esc (Goodrich et al., *Nature*, 386(6620):44-51 (1997)), Grossniklaus et al., *Science*, 280(5362):446-50 (1998); Ohad et al., *Plant Cell*, 11(3):407-16 (1999)). *Arabidopsis* contains three E(z)-like genes, curly leaf (clf), Medea (Mea) and E(z)-likeA1 (EZA1) and one esc homolog, fertilization-independent endosperm (FIE1).

Clf mutants display curled leaves, altered maturation times and partial homeotic transformations of floral tissues (Goodrich et al., *Nature*, 386(6620):44-51 (1997)). Ectopic expression is also observed for the hometoic genes Agamous (AG) and Apetela3 (AP3). These genes are specifically expressed in floral tissues where clf mRNA is also present. This indicates that, similar to the *Drosophila* PcG proteins, the presence of CLF protein is not sufficient to repress AG and AP3 transcription but requires targeting factors (Goodrich et al., *Nature*, 386(6620):44-51 (1997)). The homeotic genes AG and AP3 are also ectopically expressed in *Arabidopsis* plants with reduced methylation levels (Finnegan et al., *Proc. Natl. Acad. Sci. USA*, 93(16):8449-8454 (1996)).

Medea was identified in a screen for *Arabidopsis* gametophyte lethal mutations (Grossniklaus et al., *Science*, 280(5362):446-50 (1998); Chaudhury et al., *Proc. Natl. Acad. Sci.*, USA, 94(8):4223-8 (1997); Luo et al., *Proc. Natl. Acad. Sci. USA*, 96(1):296-301 (1999)). A plant heterozygous for mea mutations will produce 50% aborted seeds that collapse and do not germinate. Subsequently it has been found that MEA exhibits an imprinted pattern of gene expression (Kinoshita et al., *Plant Cell*, 11(10):1945-52 (1999)); Vielle-Calzada et al., *Genes Dev.*, 13(22):2971-82 (1999)). The maternal copy of Medea is expressed while the paternal copy is not. Medea mutants will allow endosperm development to occur in the absence of fertilization (Kiyosue et al., *Proc. Natl. Acad. Sci. USA*, 96(7):4186-91 (1999)). These results indicate that maternal expression of Medea is required to repress endosperm development. Due to the early lethality of Medea mutants, roles for Medea later in plant development have not been determined. A third E(z)-like gene, EZA1 is present in the *Arabidopsis* genome (Preuss, D., *Plant Cell.*, 11(5):765-8 (1999)). Presently, the function of EZA1 is unknown.

Mutations in the *Arabidopsis* esc-like gene, FIE, have phenotypes similar to Medea. A female gametophyte with a FIE mutant allele will undergo replication of the central cell nucleus and endosperm development without a fertilization event (Ohad et al., *Plant Cell*, 11(3):407-16 (1999)). This indicates that FIE is critical in the repression of endosperm development. As with Medea, due to the early lethality of FIE mutants, the role of FIE in later developmental events has not been determined. The similar phenotypes of FIE and mea mutants suggests that these two genes may interact functionally like E(z) and esc homologs in other organisms.

SUMMARY OF THE INVENTION

In one embodiment, the present invention relates to an isolated and purified nucleic acid comprising a polynucleotide selected from the group consisting of SEQ ID NO:1, SEQ ID NO:3 and conservatively modified and polymorphic variants thereof. In addition, the present invention relates to an isolated and purified nucleic acid comprising a polynucleotide having at least 60%, 70%, 80%, 90%, or 95% identity to a polynucleotide selected from the group consisting of SEQ ID NO:1 and SEQ ID NO:3.

In yet another embodiment, the present invention relates to an isolated and purified polypeptide comprising an amino acid sequence selected from the group consisting of SEQ ID NO:2, SEQ ID NO:4 and conservatively modified variants thereof. In addition, the present invention relates to an isolated and purified polypeptide comprising an amino acid sequence having at least 60%, 70%, 80% or 95% identity to an amino acid sequence selected from the group consisting of: SEQ ID NO:2 and SEQ ID NO:4.

In yet a further embodiment, the present invention relates to an expression cassette containing a promoter sequence operably linked to an isolated and purified nucleic acid comprising a polynucleotide selected from the group consisting of SEQ ID NO:1, SEQ ID NO:3 and conservatively modified and polymorphic variants thereof. Preferably, the expression cassette also contains a polyadenylation signal which is operably linked to the previously described nucleic acid. Examples of promoters which can be used in the expression cassette include constitutive and tissue specific promoters.

In yet another embodiment, the present invention relates to a bacterial cell containing the hereinbefore described expression cassette. The bacterial cell can be an *Agrobacterium tumefaciens* cell or an *Agrobacterium rhizogenes* cell.

In still yet another embodiment, the present invention relates to a plant cell transformed with the hereinbefore described expression cassette, a transformed plant containing such a plant cell, and to seed obtained from such a transformed plant. The plant cell, transformed plant and seed can be from *Zea mays L.*

BRIEF DESCRIPTION OF THE FIGURES

FIG. 1 shows the Mez1 polynucleotide and amino acid sequences. FIG. 1A shows that the polynucleotide sequence (SEQ ID NO: 1) of the Mez1 cDNA is 3180 base pairs (bp). A solid underline indicates that the putative start codon and the first in-frame stop codon is indicated with a wavy underline. FIG. 1B shows the 931 amino acid Mez1 protein (SEQ ID NO: 2).

FIG. 2 shows the Mez2 polynucleotide and amino acid sequences. FIG. 2A shows that the polynucleotide sequence (SEQ ID NO: 3) of the Mez2 cDNA is 3030 bp. The putative start codon is indicated by a solid underline while the stop codon is indicated by a wavy underline. The location of several introns is indicated by open arrowheads above the sequence. These introns were identified by sequencing of PCR products amplified from genomic DNA corresponding to bp2032 to bp2587 of the cDNA. The location of the four Mu insertions are indicated by black arrowheads below the sequence. The Mez2-Mu1 allele contains a Mu element inserted into intron 1. The location of the Mez2-Mu2, Mez2-Mu3 and Mez2-Mu4 Mu insertions are all located in exons. The nucleotides that flank the sequence that are removed by alternative splicing are indicated by a double underline. FIG. 2B shows the 893 amino acid Mez2 protein (SEQ ID NO: 4).

FIG. 3 shows the alignment of Mez1 (SEQ ID NO: 2) and Mez2 (SEQ ID NO: 4). The Mez1 (SEQ ID NO: 2) and Mez2 (SEQ ID NO: 4) protein sequences were aligned using ClustalW. These alignments were then processed using Boxshade to highlight identical residues in black and similar residues in gray. The two proteins are 42% identical and 56% similar over their entire length.

Figure 4:
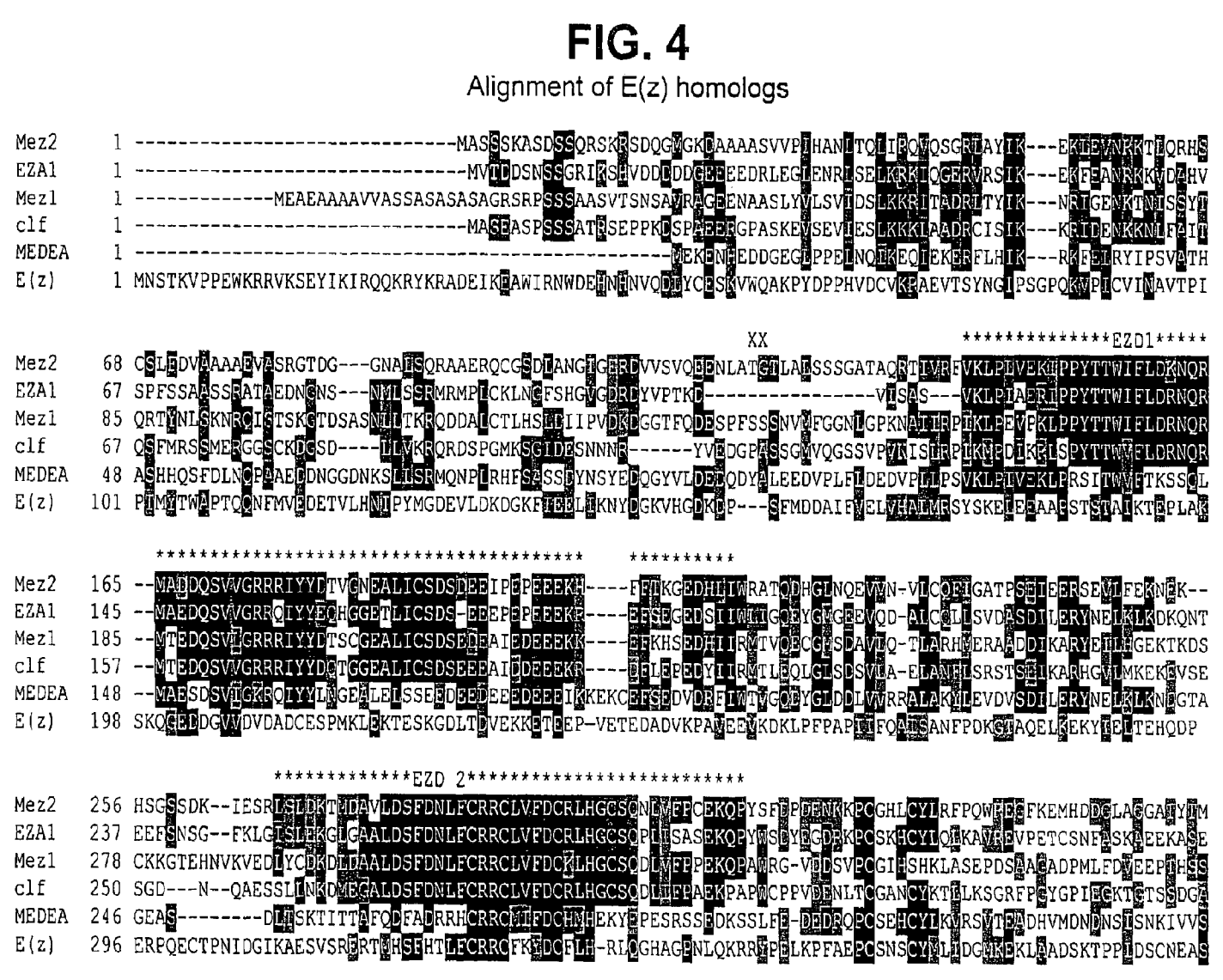
Figure 4:
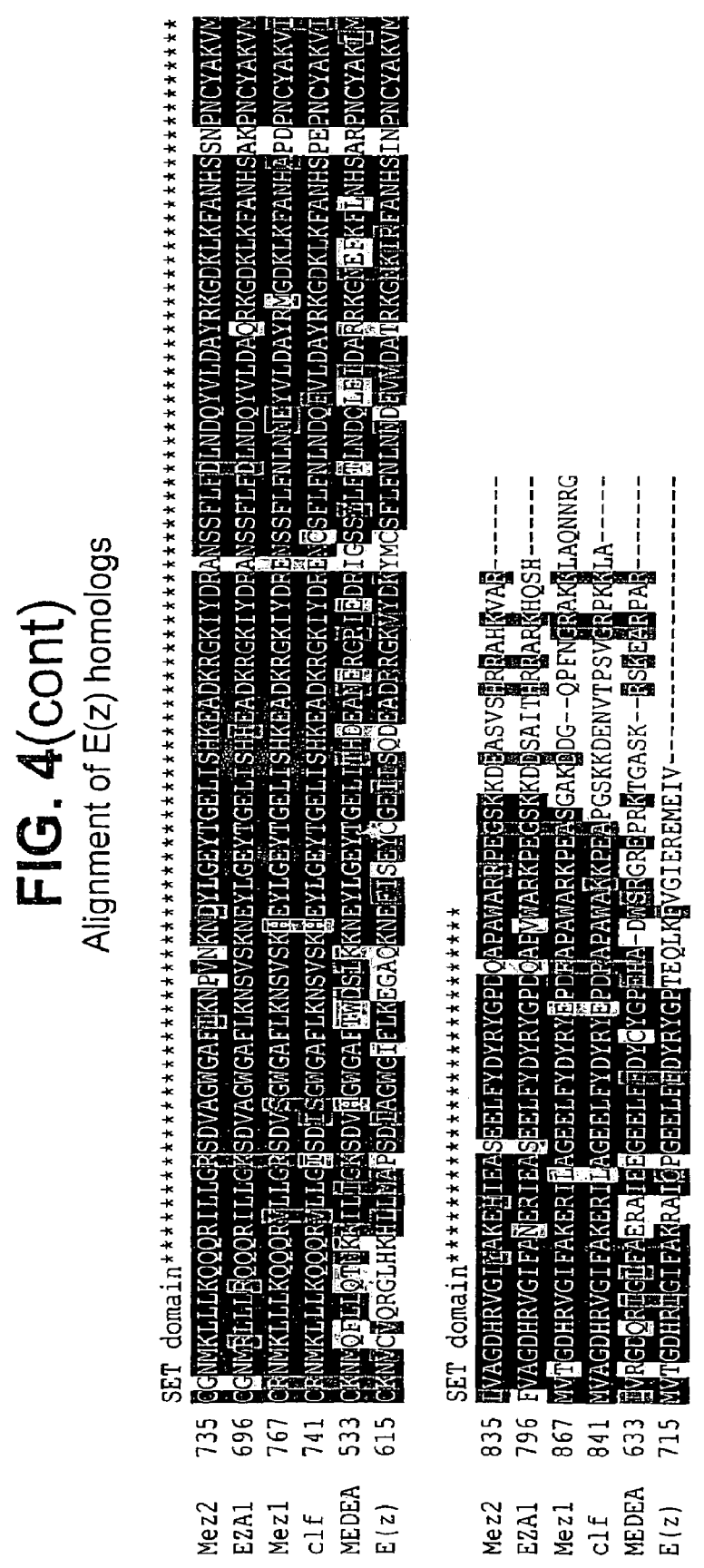

FIG. 4 shows the alignment of E(z) sequences. The sequences of *Drosophila* E(z) (AAC46462) (SEQ ID NO: 24), human EZH1 (AAC50778) (SEQ ID NO: 25), human EZH2 (AAC51520) (SEQ ID NO: 26), *C. elegans* MES-2 (AAC27124) (SEQ ID NO: 27), *Arabidopsis* CLF (AAC23781) (SEQ ID NO: 28), *Arabidopsis* MEA (AAC39446) (SEQ ID NO: 29), *Arabidopsis* EZA1 (AAD09108) (SEQ ID NO: 30), Mez1 (SEQ ID NO: 2) and Mez2 (SEQ ID NO: 4) were aligned using ClustalW. The alignments were colored using Boxshade to highlight identical residues in black and conserved residues in gray. The location of a putative bipartite nuclear localization signal in the plant sequences is indicated by *'s above the alignments. # symbols are located above the cysteine-rich region. The N-terminal SET domain is indicated by + symbols above the alignment. A putative SANT DNA binding domain is shown with symbols. $ symbols are placed above all acidic amino acid residues in an acidic region near the C-terminus. A region of high conservation in the plant sequences only containing a CRRC sequence is shown with x's above the alignment. The region between the CRRC domain and the nuclear localization signal is very divergent.

FIG. 8 shows the results of a RT-PCR analysis of Mez1 (SEQ ID NO: 1) and Mez2 (SEQ ID NO: 3) expression patterns. In FIG. 8A, the primer pair Mez1F1 (SEQ ID NO: 7)-Mez1R1 (SEQ ID NO: 21) was used to amplify 2 ng of cDNA from various maize tissues. The PCR products were then separated on a 1% agarose gel stained with ethidium bromide. The arrow indicates the expected size of the PCR product. In FIG. 8B, the primer pair Mez2F4 (SEQ ID NO: 17)-Mez2R8 was used to amplify 2 ng of cDNA from various maize tissues. The arrows indicate the expected size of Mez2 (SEQ ID NO: 3), Mez2$^{as1}$ (SEQ ID NO: 5) and Mez2$^{as2}$ (SEQ ID NO: 6) isoforms. In FIG. 8C, ubiquitin primers were used to amplify 0.2 ng of cDNA from the same maize tissues as a control. The pollen cDNA did not allow the amplification of significant amounts of product indicating that the results using this cDNA are questionable.

DEFINITIONS

Figure 5:
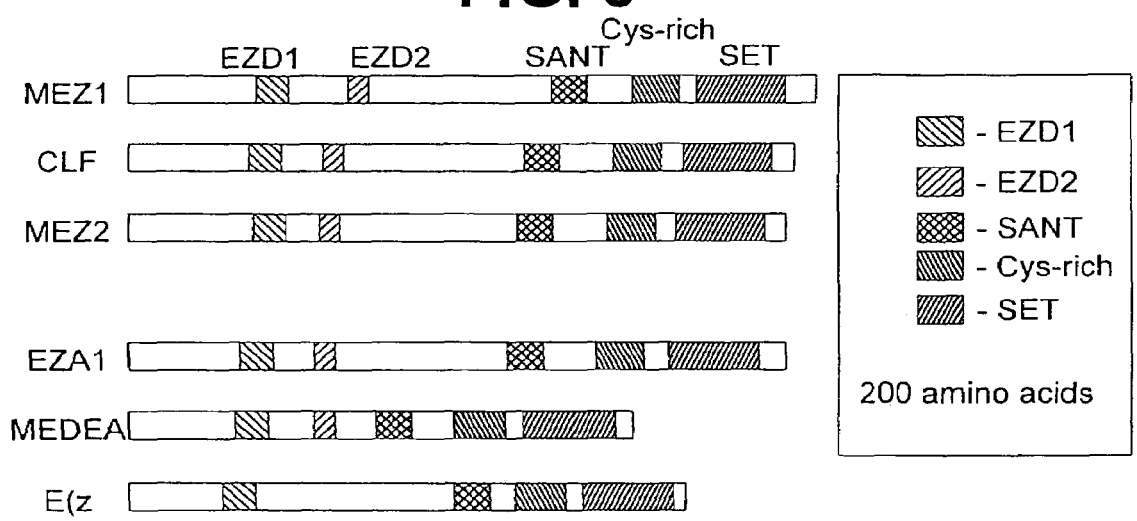
FIG. 5 shows schematic diagrams of E(z)-like proteins. E(z)-like proteins from plants and the *Drosophila* E(z) are represented by rectangles with the N-terminus located on the left for each protein. The location of the EZD1, EZD2, SANT, Cys-rich, and SET domains are indicated by shading.

Units, prefixes, and symbols can be denoted in the SI accepted form. Numeric ranges are inclusive of the numbers defining the range. Unless otherwise indicated, nucleic acids are written left to right in 5' to 3' orientation, respectively. The headings provided herein are not limitations of the various aspects or embodiments of the invention which can be had by reference to the specification as a whole. Accordingly, the terms defined immediately below are more fully defined by reference to the specification as a whole.

As used herein, the terms "amplify" or "amplified" as used interchangeably herein refer to the construction of multiple copies of a nucleic acid sequence or multiple copies complementary to the nucleic acid sequence using at least one of the nucleic acid sequences as a template. Amplification methods include the polymerase chain reaction (hereinafter "PCR"; described in U.S. Pat. Nos. 4,683,195 and 4,683,202), the ligase chain reaction (hereinafter "LCR"; described in EP-A-320,308 and EP-A-439,182), the transcription-based amplification system (hereinafter "TAS"), nucleic acid sequence based amplification (hereinafter "NASBA", Cangene, Mississauga, Ontario; described in *Proc. Natl. Acad. Sci., USA*, 87:1874-1878 (1990); *Nature*, 350 (No. 6313):91-92 (1991)), Q-Beta Replicase systems, and strand displacement amplification (hereinafter "SDA"). The product of amplification is referred to as an amplicon.

As used herein, the term "antibody" includes reference to an immunoglobulin molecule obtained by in vitro or in vivo generation of a humoral response, and includes both polyclonal and monoclonal antibodies. The term also includes genetically engineered forms such as chimeric antibodies (e.g., humanized murine antibodies), heteroconjugate antibodies (e.g., bispecific antibodies), and recombinant single chain Fc fragments (hereinafter "scFc"). The term "antibody" also includes antigen binding forms of antibodies (e.g., Fab$^1$, F(ab$^1$)$_2$, Fab, Fe, and, inverted IgG (See, Pierce Catalog and Handbook, (1994-1995) Pierce Chemical Co., Rockford, Ill.)). An antibody immunologically reactive with a particular antigen can be generated in vivo or by recombinant methods such as by the selection of libraries of recombinant antibodies in phage or similar vectors (See, e.g. Huse et al., *Science*, 246:1275-1281 (1989); and Ward, et al., *Nature*, 341:544-546 (1989); and Vaughan et al., *Nature Biotechnology*, 14:309-314 (1996)).

As used herein, the term "antisense RNA" means an RNA sequence which is complementary to a sequence of bases in the mRNA in question in the sense that each base (or the majority of bases) in the antisense sequence (read in the 3' to 5' sense) is capable of pairing with the corresponding base (G with C, A with U) in the mRNA sequence read in the 5' to 3' sense.

As used herein, the term "conservatively modified variants" applies to both amino acid and nucleic acid sequences. With respect to particular nucleic acid sequences, conservatively modified variants refers to those nucleic acids which encode identical or conservatively modified variants of the amino acid sequences. Because of the degeneracy of the genetic code, a large number of functionally identical nucleic acids encode any given protein. For example, the codons GCA, GCC, GCG and GCU all encode the amino acid alanine. Thereupon, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein which encodes a polypeptide also describes every possible "silent variation" of the nucleic acid. It is known by persons skilled in the art that each codon in a nucleic acid (except AUG, which is the only codon for the amino acid, methionine; and UGG, which is the only codon for the amino acid tryptophan) can be modified to yield a functionally identical molecule. Therefore, each silent variation of a nucleic acid which encodes a polypeptide of the present invention is implicit in each described polypeptide sequence.

With respect to amino acid sequences, persons skilled in the art will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:

1) Alanine (A), Serine (S), Threonine (T);

2) Aspartic acid (D), Glutamic acid (E);

3) Asparagine (N), Glutamine (Q);

4) Arginine (R), Lysine (K);

5) Isoleucine (I), Leucine (L), Methionine (M), Valine (V); and

6) Phenylalanine (F), Tyrosine (Y), Tryptophan (W). See also, Creighton (1984) Proteins W. H. Freeman and Company.

As used herein, the term "constitutive promoter" refers to a promoter which is active under most environmental conditions.

As used herein, the term "full length" when used in connection with a specified polynucleotide or encoded protein refers to having the entire amino acid sequence of, a native (i.e. non-synthetic), endogenous, catalytically active form of the specified protein. Methods for determine whether a sequence is full length are well known in the art. Examples of such methods which can be used include Northern or Western blots, primer extension, etc. Additionally, comparison to known full-length homologous sequences can also be used to identify full length sequences of the present invention.

As used herein, the term "heterologous" when used to describe nucleic acids or polypeptides refers to nucleic acids or polypeptides that originate from a foreign species, or, if from the same species, are substantially modified from their original form. For example, a promoter operably linked to a heterologous structural gene is from a species different from that from which the structural gene was derived, or, if from the same species, is different from any naturally occurring allelic variants.

The term "immunologically reactive conditions" as used herein, includes reference to conditions which allow an antibody, generated to a particular epitope of an antigen, to bind to that epitope to a detectably greater degree than the antibody binds to substantially all other epitopes, generally at least two times above background binding, preferably at least five times above background. Immunologically reactive conditions are dependent upon the format of the antibody binding reaction and typically are those utilized in immunoassay protocols.

As used herein, the term "inducible promoter" refers to a promoter which is under environmental control. Examples of environmental conditions that may effect transcription by inducible promoters include anaerobic conditions or the presence of light.

As used herein, the term "isolated" includes reference to material which is substantially or essentially free from components which normally accompany or interact with it as found in its naturally occurring environment. The isolated material optionally comprises material not found with the material in its natural environment. However, if the material is in its natural environment, the material has been synthetically, (e.g. non-naturally) altered by deliberate human intervention to a composition and/or placed in a locus in a cell (e.g., genome or subcellular organelle) not native to a material found in that environment.

Two polynucleotides or polypeptides are said to be "identical" if the sequence of nucleotides or amino acid residues, respectively, in the two sequences is the same when aligned (either manually for visual inspection or via the use of a computer algorithm or program) for maximum correspondence as described below. The terms "identical" or "percent identity" when used in the context of two or more polynucleotide or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. With respect to polypeptides or proteins having a "percent identity" or "percentage of sequence identity" one skilled in the art would recognize that residue positions that are not identical often differ by conservative amino acid substitutions, where amino acid residues are substituted for other amino acid residues possessing similar chemical and/or physical properties such as charge or hydrophobicity and therefore do not change the functional properties of the molecule. Where sequences differ in conservative substitutions, the percent sequence identity may be adjusted upwards to correct for the conservative nature of the substitution. Means for making this adjustment are well-known to persons skilled in the art. Typically this involves scoring a conservative substitution as a partial rather than a full mismatch, thereby increasing the percentage sequence identity.

As used herein, the term "comparison window" includes reference to a contiguous and specified segment of a polynucleotide sequence, wherein the polynucleotide sequence may be compared to a reference sequence and wherein the portion of the polynucleotide sequence in the comparison window may comprise additions or deletions (e.g., gaps) compared to the reference sequence (which does not comprise additions or deletions) for optimal alignment of the two sequences. Generally, the comparison window is at least 20 contiguous nucleotides in length, and can be 30, 40, 50, 100, or even longer. Persons skilled in the art will recognize that to avoid a high similarity to a reference sequence due to inclusion of gaps in the polynucleotide sequence a gap penalty is typically introduced and is subtracted from the number of matches.

The alignment of polynucleotide and/or polypeptide sequences for the purposes of determine sequence identity and similarity can be by either manual alignment and visual inspection or via the use of some type of computer program or algorithm. In fact, a number of computer programs are available which can be used to align polynucleotide and/or polypeptide sequences are known in the art. For example, the programs available in the Wisconsin Sequence Analysis Package, Version 9 (available from the Genetics Computer Group, Madison, Wis., 52711), such as GAP, BESTFIT, FASTA and TFASTA. For example, the GAP program is capable of calculating both the identity and similarity between two polynucleotide or two polypeptide sequences. Specifically, the GAP program uses the homology alignment algorithm of Needleman and Wunsch (J. Mol. Biol., 48:443-453 (1970)). Another example of a useful computer program is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, J. Mol. Evol., 35:351-360 (1987). Yet another example of a useful computer program that can be used for determine percent sequence identity and sequence similarity is the BLAST algorithm (Altsuchul et al., J. Mol. Biol., 215: 403-410 (1990)). The software for performing BLAST analysis is publicly available through the National Center for Biotechnology Information.

With respect to polynucleotide sequences, the term "substantial identity" means that a polynucleotide comprises a sequence that has at least 60% sequence identity, preferably at least 70% sequence identity, more preferably at least 80% sequence identity, even more preferably 90% sequence identity and most preferably at least 90% sequence identity, compared to a reference sequence using one of the alignment programs described herein conducted according to standard parameters. One skilled in the art will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, more preferably at least 70%, 80%, 90% identity, and most preferably at least 95% identity.

Polynucleotide sequences can also be considered to be substantially identical if two molecules hybridize to each other under stringent conditions. However, polynucleotides which do not hybridize to each other under stringent conditions are still substantially identical if the polypeptides which they encode are substantially identical. This can occur when a copy of a polynucleotide is created using the maximum codon degeneracy permitted by the genetic code. One indication that two polynucleotide sequences are substantially identical if the polypeptide encoded by the first nucleic acid encodes is immunologically cross reactive with the polypeptide encoded by the second polynucleotide.

With peptides, the term "substantial identity" as used herein means that a peptide comprises a sequence having at least 60% sequence identity to a reference sequence, preferably 70% sequence identity, more preferably 80% sequence identity, even more preferably 90% sequence identity, and most preferably at least 95% sequence identity to the reference sequence over a specified comparison window. Preferably, optimal alignment is conducted using the homology alignment algorithm (GAP program discussed previously) of Needleman and Wunsch, *J. Mol. Biol.*, 48: 443-453 (1990). An indication that two peptide sequences are substantially identical is that one peptide is immunologically reactive with antibodies raised against the second peptide. Thereupon, a peptide is substantially identical to a second peptide where the two peptides differ only by a conservative substitution. Peptides which are "substantially similar" share sequences as described above except that any residue positions which are not identical differ only by conservative amino acid changes.

As used herein, the term "Mez1 gene" refers to a gene of the present invention, specifically, the heterologous genomic form of a full length Mez1 polynucleotide.

As used herein, the term "Mez1 nucleic acid" refers to a nucleic acid of the present invention, specifically, a nucleic acid comprising a polynucleotide of the present invention encoding a Mez1 polypeptide (hereinafter "Mez1 polynucleotide"). An example of a Mez1 polynucleotide (cDNA) is shown in SEQ ID NO:1.

As used herein, the terms "Mez1 polypeptide", "Mez1 peptide" or "Mez1 protein" as used interchangeable herein refer to a polypeptide shown in SEQ ID NO:2. The term also includes fragments, variants, homologs, alleles or precursors (e.g., preproproteins or proproteins) thereof.

As used herein, the term "Mez2 gene" refers to a gene of the present invention, specifically, the heterologous genomic form of a full length Mez2 polynucleotide.

As used herein, the term "Mez2 nucleic acid" refers to a nucleic acid of the present invention, specifically, a nucleic acid comprising a polynucleotide of the present invention encoding a Mez2 polypeptide (hereinafter a "Mez2 polynucleotide"). An example of a Mez2 polynucleotide (cDNA) is shown in SEQ ID NO:3.

As used herein, the terms "Mez2 polypeptide", "Mez2 peptide" or "Mez2 protein" as used interchangeably herein refer to a polypeptide shown in SEQ ID NO:4. The term also includes fragments, variants, homologs, alleles or precursors (e.g., preproproteins or proproteins) thereof. A "Mez2 protein" is a protein of the present invention and comprises a Mez2 polypeptide.

As used herein, the term "nucleic acid" refers to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

As used herein, the term "nucleotide(s)" refers to a macromolecule containing a sugar (either a ribose or deoxyribose), a phosphate group and a nitrogenous base.

As used herein, the term "operably linked" includes reference to a functional linkage between a promoter and a second sequence, wherein the promoter sequence initiates and mediates transcription of the DNA sequence corresponding to the second sequence. Generally, operably linked means that the polynucleotide sequences being linked are contiguous and, where necessary to joint two protein coding regions, contiguous and in the same reading frame.

As used herein, the term "plant" includes reference to whole plants, plant organs (e.g., leaves, stems, flowers, roots, etc.), seeds and plant cells and progeny of the same. Plant cell, as used herein, includes, but is not limited to, suspension cultures, embryos, meristematic regions, callus tissue, shoots, gametophytes, sporophytes, pollen and microspores. The class of plants which can be used in the methods of the present invention are generally as broad as the class of higher plants amenable to transformation techniques, including angiosperms (monocotyledonous and dicotyledonous plants) as well as gymnosperms (e.g. *Coniferophyta* (conifers, *Cycadophyta* (cycads), *Ginkgophyta* (maidenhair tree) and *Gnetophyta* (gnetophytes)). The term "plant" as used herein also includes plants of a variety of ploidy levels, such as polyploid, diploid, haploid and hemizygous.

As used herein, the term "plant promoter" refers to a promoter capable of initiating transcription in plant cells.

As used herein, the term "polymorphic variant" in connection with a polynucleotide sequence refers to a variation in the polynucleotide sequence of a particular gene between individuals of a given species. Polymorphic variants may also encompass "single nucleotide polymorphisms" (SNPs) in which the polynucleotide sequence varies by one base. The presence of SNPs may be indicative of a certain population for a disease state or propensity for a disease state.

As used herein, the term "polynucleotide" refers to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full length or a subsequence of a native or heterologous structural or regulatory gene. Unless otherwise indicated, the term includes reference to the specified sequence as well as the complementary sequence thereof. Thereupon, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. As used herein, the term polynucleotide includes such chemically, enzymatically or metabolically modified forms of polynucleotides, as well as the chemical forms of DNA and RNA characteristic of viruses and cells, including, but not limited to, simple and complex cells.

As used herein, the terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation.

As used herein, the term "promoter" refers to a region of DNA upstream from the start of transcription and involved in recognition and binding of RNA polymerase and other proteins to initiate transcription. A promoter can optionally include distal enhancers or repressor elements which can be located several thousand base pairs from the start site of transcription.

As used herein, the term "recombinant" includes reference to a cell, or nucleic acid, or vector, that has been modified by the introduction of a heterologous nucleic acid or the alteration of a native nucleic acid to a form not native to that cell, or that the cell is derived from a cell so modified. For example, recombinant cells express genes that are not found within the native (non-recombinant) form of the cell or express native genes that are otherwise abnormally expressed, under expressed or not expressed at all.

As used herein, the term "recombinant expression cassette" is a nucleic acid construct, generated recombinantly or synthetically, with a series of specified nucleic acid elements which permit transcription of a particular nucleic acid in a target cell. The expression vector can be part of a plasmid, virus, or nucleic acid fragment. Typically, the recombinant expression cassette portion of the expression vector includes a nucleic acid to be transcribed, and a promoter.

As used herein, the terms "residue" or "amino acid" or "amino acid residue" are used interchangeably herein to refer to an amino acid that is incorporated into a protein, polypeptide or peptide. The amino acid may be a naturally occurring amino acid, and unless otherwise limited, may encompass known analogs of natural amino acids that can function in a similar manner as naturally occurring amino acids.

As used herein, the term "selective hybridization" or "selectively hybridizes" are used interchangeably herein includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, preferably 90% sequence identity, and most preferably 100% sequence identity (e.g., complementary) with each other.

As used herein, the term, "specifically binds" includes reference to the preferential association of a ligand, in whole or part, with a particular target molecule (i.e., "binding partner" or "binding moiety" relative to compositions lacking that target molecule). It is, of course, recognized that a certain degree of non-specific interaction may occur between a ligand and a non-target molecule. Nevertheless, specific binding, may be distinguished as mediated through specific recognition of the target molecule. Typically, specific binding results in a much stronger association between the ligand and the target molecule than between the ligand and non-target molecule. Specific binding by an antibody to a protein under such conditions requires an antibody that is selected for its specificity for a particular protein. The affinity constant of the antibody binding site for its cognate monovalent antigen is at least $10^7$, usually at least $10^9$, more preferably at least $10^{10}$, and most preferably at least $10^{11}$ liters/mole.

As used herein, the terms "stringent hybridization" conditions or "stringent conditions" refers to conditions under which a probe will hybridize to its target subsequence, typically in a complex mixture of nucleic acid, but to no other sequences. Stringent conditions are sequence dependent and are different under different environmental parameters. An extensive guide to hybridization of nucleic acids is found in Tijssen (1993) *Laboratory Techniques in Biochemistry and Molecular Biology-Hybridization with Nucleic Acid Probes Part* 1, Chapter 2 "Overview of Principles of Hybridization and the Strategy of Nucleic Acid Probe Assays" Elsevier, N.Y. Generally, highly stringent conditions are selected to be about 5° C.-10° C. lower than the thermal melting point ($T_m$) for the specific sequence at a defined ionic strength and pH. The $T_m$ is the temperature (under defined ionic strength and pH and nucleic concentration) at which 50% of the target sequence hybridizes to a perfectly matched probe. Stringent conditions are those in which the salt concentration is less than about 1.0M sodium ion, typically about 0.01 to 1.0M sodium ion concentration (or other salts) at a pH of 7.0 to 8.3 and at a temperature of at least about 30° C. for short probes (such as those having a length between about 10 to 50 nucleotides) and at least about 60° C. for long probes (such as those having a length greater than 50 nucleotides). In contrast, low stringency conditions are at about 15-30° C. below the $T_m$. Stringent hybridization conditions are sequence-dependent and will be different in different circumstances. Longer sequences hybridize at higher temperatures.

As used herein, the term "tissue-specific promoter" includes reference to a promoter in which expression of an operably linked gene is limited to a particular tissue or tissues.

As used herein, the term "transgenic plant" includes reference to a plant modified by introduction of a heterologous polynucleotide. Generally, the heterologous polynucleotide is a Mez1 or Mez2 structural or regulatory gene or subsequences thereof.

SEQUENCE LISTINGS

The present application also contains a sequence listing that contains thirty (30) sequences. The sequence listing contains nucleotide sequences and amino acid sequences. For the nucleotide sequences, the base pairs are represented by the following base codes:

| Symbol | Meaning |
|---|---|
| A | A; adenine |
| C | C; cytosine |
| G | G; guanine |
| T | T; thymine |
| U | U; uracil |
| M | A or C |
| R | A or G |
| W | A or T/U |
| S | C or G |

| Symbol | Meaning |
|---|---|
| Y | C or T/U |
| K | G or T/U |
| V | A or C or G; not T/U |
| H | A or C or T/U; not G |
| D | A or G or T/U; not C |
| B | C or G or T/U; not A |
| N | (A or C or G or T/U) |

The amino acids shown in the application are in the L-form and are represented by the following amino acid-three letter abbreviations:

| Abbreviation | Amino acid name |
|---|---|
| Ala | L-Alanine |
| Arg | L-Arginine |
| Asn | L-Asparagine |
| Asp | L-Aspartic Acid |
| Asx | L-Aspartic Acid or Asparagine |
| Cys | L-Cysteine |
| Glu | L-Glutamic Acid |
| Gln | L-Glutamine |
| Glx | L-Glutamine or Glutamic Acid |
| Gly | L-Glycine |
| His | L-Histidine |
| Ile | L-Isoleucine |
| Leu | L-Leucine |
| Lys | L-Lysine |
| Met | L-Methionine |
| Phe | L-Phenylalanine |
| Pro | L-Proline |
| Ser | L-Serine |
| Thr | L-Threonine |

-continued

| Abbreviation | Amino acid name |
|---|---|
| Trp | L-Tryptophan |
| Tyr | L-Tyrosine |
| Val | L-Valine |
| Xaa | L-Unknown or other |

Introduction

The present invention is based, at least in part, on the discovery and cloning of two (2) PcG genes from *Zea mays* L. (maize) termed the Mez1 gene and the Mez2 gene. The protein encoded by the Mez1 gene has been mapped to chromosome 6 (bin 6.01-6.02) and the protein for the Mez2 gene has been mapped to chromosome 9 (bin 9.04).

The present invention is applicable to a broad range of types of plants, including, but not limited to, *Zea mays L., Oryza sativa, Secale cereale, Triticum aestivum, Daucus carota, Brassica oleracea, Cucumis melo, Cucumis sativus, Latuca sativa, Solanum tubersoum, Lycopersicon esculentum, Phaseolus vulgaris*, and *Brassica napus*.

Nucleic Acids

In one embodiment, the present invention relates to isolated nucleic acids of DNA, RNA, and analogs and/or chimeras thereof, comprising a polynucleotide, wherein said polynucleotide is a Mez1 or Mez2 polynucleotide which encodes a polypeptide of SEQ ID NO:2 (a Mez1 polypeptide) or SEQ ID NO:4 (a Mez2 polypeptide), and conservatively modified variants thereof. It is known in the art that the degeneracy of the genetic code allows for a plurality of polynucleotides to encode for the identical amino acid sequence. These "silent variations", as they are common referred to, can be used to selectively hybridize and detect polymorphic variants of the polynucleotides of the present invention.

An example of a Mez1 polynucleotide which encodes the Mez1 polypeptide of SEQ ID NO:2 is shown in SEQ ID NO:1. The polynucleotide of SEQ ID NO:1 is 3180 base pairs in length.

An example of a Mez2 polynucleotide which encodes the Mez2 polypeptide of SEQ ID NO:4 is shown in SEQ ID NO:3. The polynucleotide of SEQ ID NO:3 is 3030 base pairs in length.

Figure 7:
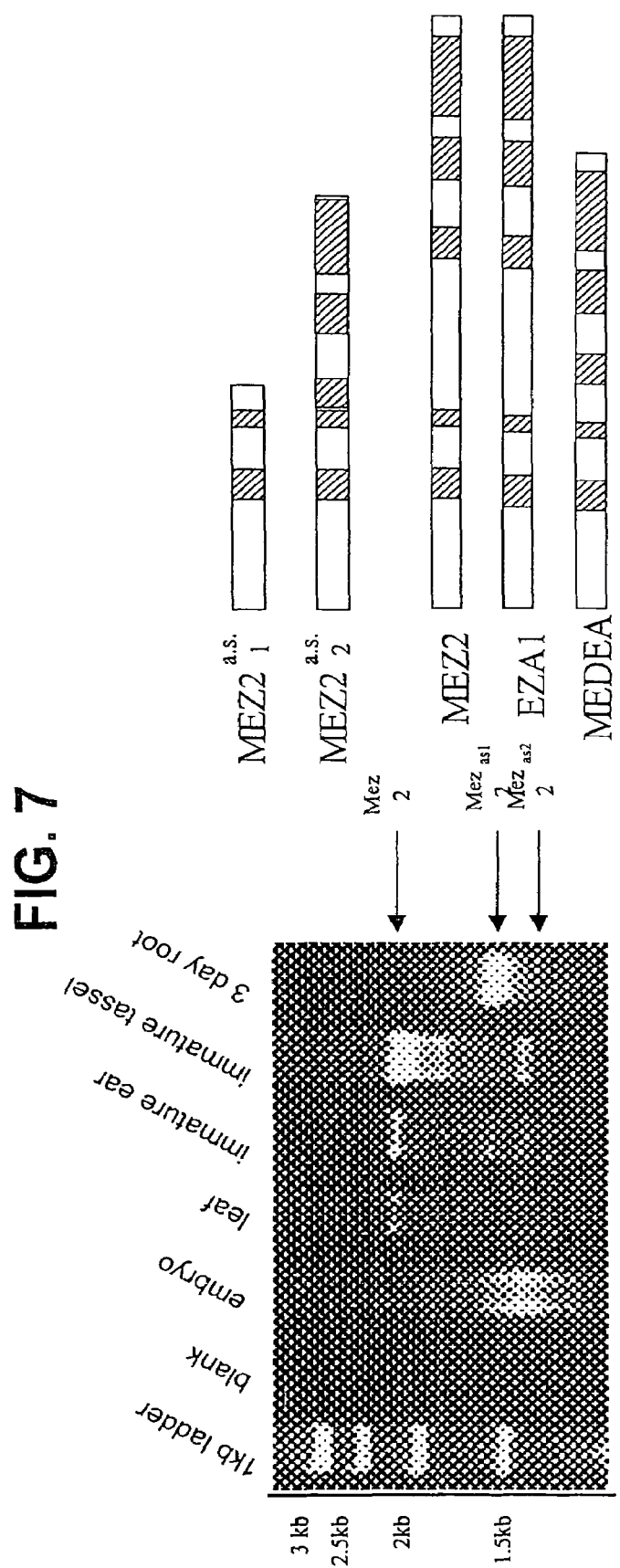
FIG. 7 shows that the Mez2 transcript is alternatively spliced in different tissues. Three predominant transcripts are found, the full length transcript and two smaller transcripts. The two smaller transcripts were isolated and sequenced to reveal the difference between the transcripts. The Mez2$^{a.s.2}$ transcript (SEQ ID NO: 6) is lacking base pairs 1016 to 1676 and translation of this sequence results in a truncated protein of 341 amino acids lacking the conserved C-terminal domains. The Mez2$^{a.s.2}$ transcript (SEQ ID NO: 6) is lacking base pairs 1016 to 1827 and translation of this sequence results in a 624 amino acid protein that lacks the large variable region from the middle of the Mez2 protein (SEQ ID NO: 4). The Mez2$^{a.s.2}$ transcript (SEQ ID NO: 6) has been found as the predominant transcript in embryo and endosperm tissues.

The Mez2 polynucleotide of SEQ ID NO:3, in addition to encoding for the Mez2 polypeptide, contains two (2) alternative splice sites. These alternative splice sites are referred to herein as Mez2 alternative splice 1 ("Mez2$^{as1}$") (SEQ ID NO:5) and Mez2 alternative splice 2 ("Mez2$^{as2}$") (SEQ ID NO:6). The polynucleotide sequence of Mez2$^{as1}$ (hereinafter Mez2$^{as1}$ polynucleotide") is identical to the Mez2 polynucleotide of SEQ ID NO:3 except that Mez2$^{as1}$ polynucleotide is missing a fragment of 659 basepairs in length. Specifically, this deleted fragment corresponds to 1016 to 1676 in the Mez2 polynucleotide of SEQ ID NO:3. The Mez2$^{as1}$ polynucleotide deletion causes a frameshift and a truncated protein of 341 amino acids which is missing the SANT, nuclear localization signal, cysteine rich region and SET domains (See FIG. 7).

The polynucleotide sequence of Mez2$^{as2}$ (hereinafter Mez2$^{as2}$ polynucleotide") is identical to the Mez2 polynucleotide of SEQ ID NO:3 except that Mez2$^{as2}$ polynucleotide is missing a fragment of 810 basepairs in length. Specifically, this deleted fragment corresponds to 1016 to 1827 in the Mez2 polynucleotide of SEQ ID NO:3. The Mez2$^{as2}$ polynucleotide deletion does not result in a frameshift. The deletion in Mez2$^{as2}$ results in a 624 amino acid protein that is missing the SANT domain (See FIG. 7).

In another embodiment, the present invention also provides isolated nucleic acids comprising polynucleotides encoding conservatively modified variants of a Mez1 or Mez2 polypeptides of SEQ ID NOS:2 and 4. Such conservatively modified variants can be used for a number of useful purposes, such as, but not limited to, the generation or selection of antibodies immunoreactive to the non-variant polypeptide. Also, in yet another embodiment, the present invention also relates to isolated nucleic acids comprising polynucleotides encoding one or more polymorphic variants of polypeptides/polynucleotides. Polymorphic variants are used to follow the segregation of chromosome regions and are typically used in marker assisted selection methods for crop improvement.

In another embodiment, the present invention relates to the isolation nucleic acids comprising polynucleotides of the present invention which selectively hybridize, under selective hybridization conditions (i.e. stringent hybridization conditions), to the Mez1 (SEQ ID NO: 1) or Mez2 (SEQ ID NO: 3) polynucleotide. The isolation of such nucleic acids can be accomplished by a number of techniques. For example, oligonucleotide probes based upon the Mez1 (SEQ ID NO: 1) and Mez2 (SEQ ID NO: 3) polynucleotides described herein can be used to identify, isolate or amplify partial or full length clones in a deposited library (such as a cDNA or genomic DNA library). For example, a cDNA or genomic library can be screened using a probe based upon the sequence of the Mez1 (SEQ ID NO: 1) or Mez2 (SEQ ID NO: 3) polynucleotides described herein. These probes can be used to hybridize with genomic DNA or cDNA sequences to isolate homologous genes in the same or different plant species.

Alternatively, nucleic acids of interest can be amplified from nucleic acid samples using various amplification techniques known in the art. For example, PCR can be used to amplify the sequences of the Mez1 or Mez2 genes directly from genomic DNA, from cDNA, from genomic libraries or cDNA libraries. PCR and other in vitro amplification methods (such as LCR, etc.) can be used to clone nucleic acid sequences that code for proteins to be expressed, to make nucleic acids for use as probes for detecting the presence of the desired mRNA in samples, for nucleic acid sequencing or for other purposes.

In yet another embodiment, the present invention relates to isolated nucleic acid comprising polynucleotides, wherein the polynucleotides of said nucleic acid have a specified identity at the nucleotide level to the previously described Mez1 (SEQ ID NO: 1) or Mez2 (SEQ ID NO: 3) polynucleotides. The percentage of identity is at least 60%, preferably 70%, more preferably 80%, even more preferably 90% and most preferably 95%.

In yet another embodiment, the present invention relates to isolated nucleic acids comprising polynucleotides complementary to the previously described Mez1 (SEQ ID NO: 1) or Mez2 (SEQ ID NO: 3) polynucleotides. One skilled in the art will recognize that complementary sequences will base pair throughout their entire length with the previously described Mez1 (SEQ ID NO: 1) or Mez2 (SEQ ID NO: 3) polynucleotides (meaning that they have 100% sequence identity over their entire length). Complementary bases associate through hydrogen bonding in double stranded nucleic acids. Base pairs known to be complementary include the following: adenine and thymine, guanine and cytosine and adenine and uracil.

In yet another embodiment, the present invention relates to isolated nucleic acids comprising polynucleotides which comprise at least 15 contiguous bases from the previously described Mez1 (SEQ ID NO: 1) or Mez2 (SEQ ID NO: 3) polynucleotides. More specifically, the length of the polynucleotides can be from about 15 contiguous bases to the length of the Mez1 (SEQ ID NO: 1) or Mez2 (SEQ ID NO: 3) polynucleotide from which the polynucleotide is a subsequence of. For example, such polynucleotides can be 15, 35, 55, 75, 95, 100, 200, 400, 500, 750, etc. contiguous nucleotides in length from the previously described Mez1 (SEQ ID NO: 2) or Mez2 (SEQ ID NO: 4) polypeptide. In addition, such subsequences can optionally comprise or lack certain structural characteristics from the Mez1 (SEQ ID NO: 1) or Mez2 (SEQ ID NO: 3) polynucleotides from which it is derived.

Polypeptides

In one embodiment, the present invention relates to a Mez1 polypeptide of SEQ ID NO:2. The Mez1 polypeptide is 931 amino acids in length, has a molecular weight of about 103.75 kDa and an isoelectric point of 8.91.

In a second embodiment, the present invention relates to a Mez2 polypeptide of SEQ ID NO:4. The Mez2 polypeptide is 893 amino acids in length, has a molecular weight of about 100.01 kDa and an isoelectric point of 8.47.

The Mez1 (SEQ ID NO: 2) and Mez2 (SEQ ID NO: 4) polypeptides contain a number of domains. These domains are: EZD1, EZD2, SANT domain, cysteine rich region and SET domain (See, FIG. 5). The EZD1 and EZD2 regions are conserved domains specific to the E(z) family. EZD1 is a highly conserved acidic region of 74 amino acids in the N-terminal region. The EZD1 domain contains a significant proportion of charged residues (34-39%) with seven more acidic residues than basic residues. The function of this domain is presently not known. The EZD1 is highly conserved between Mez1 (SEQ ID NO: 2), Mez2 (SEQ ID NO: 4), clf (SEQ ID NO: 28), and EZA1 (SEQ ID NO: 30). EZD2 is a small, highly conserved region of 44 amino acids near amino acid 250 of the plant and animal E(z)-like proteins. The EZD2 region is composed primarily of polar or charged residues. There are two (2) regions near the C-terminus of these protein are well conserved among all E(z) proteins (See FIG. 5). These are the cysteine rich region and the SET domain. The Cys-rich region has fifteen invariant cysteine residues with a conserved spacing pattern in all E(z) homologs. The spacing of the cysteine residues in all E(z) homologs is unique and is different from other Cys-rich zinc finger domains involved in DNA binding. The function of the cysteine rich domain is not known but it is highly conserved among all E(z)-like genes. The SET domain is also highly conserved and is believed to be involved in mediating protein-protein interactions (Cui et al., *Nat. Genet.*, 18:331-337 (1998); Huang et al., *J. Biol. Chem.*, 273:15933-15939 (1998)). The SANT binding domain is often involved in non-specific DNA binding (Aasland, R., et al., *Trends Biochem. Sci.*, 21(3):8-88 (1996)).

In another embodiment, the present invention relates to a polypeptide having a specified percentage of sequence identity with the Mez1 (SEQ ID NO: 2) or Mez2 (SEQ ID NO: 4) polypeptide of the present invention. The percentage of sequence identity is at least 60%, preferably 70%, more preferably 80%, even more preferably 90% and most preferably 95%.

The present invention also provides antibodies which specifically react with the Mez1 (SEQ ID NO: 2) or Mez2 (SEQ ID NO: 4) polypeptides of the present invention under immunologically reactive conditions. An antibody immunologically reactive with a particular antigen can be generated in vivo or by recombinant methods such as by selection of libraries of recombinant antibodies in phage or similar vectors.

Many methods of making antibodies are known to persons skilled in the art. A number of immunogens can be used to produce antibodies specifically reactive to the isolated Mez1 (SEQ ID NO: 2) or Mez2 (SEQ ID NO: 4) polypeptides of the present invention under immunologically reactive conditions. An isolated recombinant, synthetic, or native isolated Mez1 or Mez2 polypeptide of the present invention is the preferred immunogen (antigen) for the production of monoclonal or polyclonal antibodies.

The Mez1 or Mez2 polypeptide can be injected into an animal capable of producing antibodies. Either monoclonal or polyclonal antibodies can be generated for subsequent use in immunoassays to measure the presence and quantity of the Mez1 (SEQ ID NO: 2) or Mez2 (SEQ ID NO: 4) polypeptide. Methods of producing monoclonal or polyclonal antibodies are known to persons skilled in the art (See, Coligan, *Current Protocols in Immunology* Wiley/Greene, NY (1991); Harlow and Lane, *Antibodies. A Laboratory Manual* Cold Spring Harbor Press, NY (1989)); and Goding *Monoclonal Antibodies: Principles and Practice* (2d ed.) Academic Press, New York, N.Y. (1986)).

The Mez1 or Mez2 polypeptides and antibodies can be labeled by joining, either covalently or non-covalently, a substance which provides for a detectable signal. A wide variety of labels and conjugation techniques are known to persons skilled in the art. Suitable labels include radionucleotides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241.

The antibodies of the present invention can be used to screen plants for the expression of the Mez1 (SEQ ID NO: 2) or Mez2 (SEQ ID NO: 4) polypeptides of the present invention. The antibodies of the present invention can also be used for affinity chromatography for the purpose of isolating Mez1 (SEQ ID NO: 2) or Mez2 (SEQ ID NO: 4) polypeptides.

The present invention further provides Mez1 (SEQ ID NO: 2) or Mez2 (SEQ ID NO: 4) polypeptides that specifically bind, under immunologically reactive conditions, to an antibody generated against a defined immunogen, such as an immunogen consisting of the Mez1 or Mez2 polypeptides. Immunogens will generally have a length of at least 10 contiguous amino acids from the Mez1 (SEQ ID NO: 2) or Mez2 (SEQ ID NO: 4) polypeptides of the present invention, respectively.

A variety of immunoassay formats are appropriate for selecting antibodies specifically reactive with a particular protein. For example, solid-phase ELISA immunoassays are routinely used to select monoclonal antibodies specifically reactive with a protein (See Harlow and Lane, *Antibodies, A Laboratory Manual*, Cold Spring Harbor Publications, New York (1988), for a description of immunoassay formats and conditions that can be used to determine specific reactivity). The antibody may be polyclonal but preferably is monoclonal. Generally, antibodies cross-reactive to Mez1 (SEQ ID NO: 2) or Mez2 (SEQ ID NO: 4) polypeptides are removed by immunoabsorption.

Immunoassays in the competitive binding format are typically used for cross-reactivity determinations. For example, an immunogenic Mez1 or Mez2 polypeptide can be immobilized to a solid support. Polypeptides added to the assay compete with the binding of the antisera to the immobilized antigen. The ability of the above polypeptides to compete with the binding of the antisera to the immobilized Mez1 or Mez2 polypeptide is compared to the immunogenic Mez1 or Mez2 polypeptide. The percent cross-reactivity for the above proteins is calculated, using standard calculations known to persons skilled in the art.

The immunoabsorbed and pooled antisera are then used in a competitive binding immunoassay to compare a second "target" polypeptide to the immunogenic polypeptide. In order to make this comparison, the two polypeptides are each assayed at a wide range of concentrations and the amount of each polypeptide required to inhibit 50% of the binding of the antisera to the immobilized protein is determined using standard techniques. If the amount of the target polypeptide required is less than twice the amount of the immunogenic polypeptide that is required, then the target polypeptide is said to specifically bind to an antibody generated to the immunogenic protein. As a final determination of specificity, the pooled antisera is fully immunoabsorbed with the immunogenic polypeptide until no binding to the polypeptide used in the immunoabsorption is detectable. The fully immunoabsorbed antisera is then tested for reactivity with the test polypeptide. If no reactivity is observed, then the test polypeptide is specifically bound by the antisera elicited by the immunogenic protein.

Production of Recombinant Expression Cassettes

Isolated nucleic acids of the present invention can be used in recombinant expression cassettes. One of ordinary skill in the art will recognize that a nucleic acid used in the recombinant expression cassettes described herein encoding a functional Mez1 or Mez2 polypeptide need not have a sequence identical to the exemplified nucleic acids disclosed herein and does not need to be full length, so long as the desired functional domain of the Mez1 or Mez2 protein is expressed.

A nucleic acid comprising a polynucleotide coding for the desired functional Mez1 or Mez2 polypeptide, for example a cDNA or a genomic sequence encoding a full length protein, can be used to construct a recombinant expression cassette which can be introduced into a desired plant. An expression cassette will typically comprise the functional Mez1 or Mez2 nucleic acid operably linked in either the sense or antisense direction to transcriptional and translational initiation regulatory sequences which will direct the transcription of the sequence from the functional Mez1 or Mez2 nucleic acid in the intended tissues for the transformed plant. Examples of transcriptional and translational initiation regions that can be used in the recombinant expression cassette are well known in the art.

The recombinant expression cassette will contain a promoter which is used to direct expression of the polynucleotides of the present invention in one, more than one, or in all of the tissues of a regenerated plant. For example, a constitutive plant promoter may be employed which will direct expression of the functional Mez1 or Mez2 polypeptide in all tissues of a regenerated plant. Examples of constitutive promoters includes, but is not limited to, the cauliflower mosaic virus (hereinafter "CaMV") 35S transcription initiation region, the NOS promoter, the RUBISCO promoter, the 1' or 2'—promoter derived from T-DNA of *Agrobacterium tumefaciens*, etc. The determination of a suitable constitutive plant promoter to be used in the recombinant expression cassette can readily be determined by persons skilled in the art.

Alternatively, an inducible plant promoter can be used. An inducible plant promoter may direct expression of the Mez1 or Mez2 nucleic acid in specific tissue or under more precise environmental or developmental control in a regenerated plant. Examples of environmental conditions that may effect transcription by inducible promoters include pathogen attack, anaerobic conditions, or the presence of light. Examples of inducible promoters include, but are not limited to, the Hsp70 promoter (which is inducible by heat stress), the PPDK promoter (which is inducible by light), etc.

Promoters derived from the Mez1 or Mez2 genes can be used to direct expression. These promoters can also be used to direct expression of heterologous sequences. The promoters can be used, for example, in recombinant expression cassettes to drive expression of the Mez1 or Mez2 nucleic acids of the present invention or heterologous sequences.

Such promoters can be identified as follows. The 5' portions of the Mez1 or Mez2 genes described herein are analyzed for sequences characteristic of promoter sequences. For instance, promoter sequence elements include the TATA box consensus sequence (TATAAT), which is usually 20 to 30 base pairs upstream of the transcription start site. In plants, further upstream from the TATA-box, at positions −80 to −100, there is typically a promoter element with a series of adenines surrounding the trinucleotide G (or T) N G. (See, J. Messing et al., in *Genetic Engineering in Plants*, pp. 221-227 (Kosage, Meredith and Hollaender, eds. 1983)).

If proper polypeptide expression is desired, a polyadenylation region at the 3'-end of the Mez1 or Mez2 polynucleotide coding region should be included. The polyadenylation region can be derived from a natural gene, from a variety of other plant genes, or from T-DNA. For example, polyadenylation regions can be derived from the nopaline synthase or octopine synthase genes.

The expression cassette comprising the Mez1 or Mez2 nucleic acids will typically comprise one or more marker genes which confers a selectable phenotype on plant cells. For example, the marker gene can encode biocide resistance, particularly antibiotic resistance, such as resistance to kanamycin, G418, bleomycin, hygromycin, or herbicide resistance, such as resistance to chlorosulforon.

As discussed briefly above, the Mez1 or Mez2 nucleic acids can be inserted into a recombinant expression cassette in the antisense direction. Expression of the Mez1 or Mez2 nucleic acid in antisense direction will result in the production of antisense RNA. It is well known to persons skilled in the art that a cell manufactures protein by transcribing the DNA of the gene encoding a protein to produce RNA, which is then processed to messenger RNA (hereinafter "mRNA") (e.g., by the removal of introns) and finally translated by ribosomes into protein. This process may be inhibited in the cell by the presence of antisense RNA. It is believed that this inhibition takes place by formation of a complex between the two complementary strands of RNA, thus preventing the formation of protein. It is presently unclear how this mechanism works. However, it is believed that the complex may interfere with further translation, degrade the mRNA, or have more than one of these effects. This antisense RNA can be produced in the cell by transformation of the cell with an appropriate recombinant expression cassette designed to transcribe the non-template strand (as opposed to the template strand) of the relevant gene (or of a nucleic acid sequence showing substantial identity therewith).

The use of antisense RNA to downregulate the expression of specific plant genes is well known. Reduction in gene expression has been determined to led to changes in the phenotype of a plant, either at the level of gross visible phenotypic difference (see van der Krol et al., *Nature*, 333:866-869 (1988)), or at a more subtle biochemical level (Smith et al., *Nature*, 334:724-726 (1988)). Another method for inhibiting gene expression in transgenic plants involves the use of sense RNA transcribed from an exogenous template to downregulate the expression of specific plant genes (See, Jorgensen, Keystone Symposium "Improved Crop and Plant Products through Biotechnology", Abstract X1-022 (1994)). Thereupon, both antisense and sense RNA can be used to achieve downregulation of gene expression in plants, which are encompassed by the present invention.

Production of Transgenic Plants

Techniques for transforming a wide variety of higher plant species using the recombinant expression cassettes hereinbefore described are well known and described in the technical and scientific literature (See, for example, Weising et al., *Ann. Rev. Genet.*, 22:421-477 (1988)).

The hereinbefore described recombinant expression cassettes can be introduced into the genome of a desired plant host by a variety of conventional techniques which are well known to persons skilled in the art. For example, the recombinant expression cassette can be introduced directly into the genomic DNA of the plant cell using techniques such as electroporation, PEG poration, particle bombardment, silicon fiber delivery, and microinjection of plant cell protoplasts or embryogenic callus, or the expression cassettes can be introduced directly to plant tissue using ballistic methods, such as DNA particle bombardment. Alternatively, the expression cassettes may be combined with suitable T-DNA flanking regions and introduced into a conventional *Agrobacterium tumefaciens* or *Agrobacterium rhizogenes* host vector. The virulence functions of the *Agrobacterium* host will direct the insertion of the expression cassette and adjacent marker gene into the plant cell DNA when the cell is infected by the bacteria.

Plants which can be transformed with the recombinant expression cassette of the present invention include, but are not limited to, *Zea mays* L., *Oryza sativa*, *Secale cereale*, *Triticum aestivum*, *Daucus carota*, *Brassica oleracea*, *Cucumis melo*, *Cucumis sativus*, *Latuca sativa*, *Solanum tubersoum*, *Lycopersicon esculentum*, *Phaseolus vulgaris*, *Brassica napus*, etc.

Transformation techniques are well known to persons skilled in the art. For example, the introduction of expression cassettes using polyethylene glycol precipitation is described in Paszkowski et al., *EMBO J.*, 3:2712-2722 (1984). Electroporation techniques are described in Fromm et al., *Proc. Natl. Acad. Sci. USA*, 82:5824 (1985). Biolistic transformation techniques are described in Klein et al., *Nature*, 327:70-73 (1987).

*Agrobacterium tumefaciens*-mediated transformation techniques are well known to persons skilled in the art (See, for example Horsch et al., *Science* 233:496-498 (1984), and Fraley et al., *Proc. Natl. Acad. Sci. USA*, 80:4803 (1983)). Although *Agrobacterium* is useful primarily in dicots, certain monocots can be transformed by *Agrobacterium*. U.S. Pat. No. 5,550,318 describes *Agrobacterium* transformation of maize.

Moreover, the following methods of transfection or transformation can also be used: (a) *Agrobacterium rhizogenes*-mediated transformation (See, Lichtenstein and Fuller In *Genetic Engineering*, vol. 6, P W J Rigby, Ed., London, Academic Press, (1987)); (b) liposome-mediated DNA uptake (See, Freeman et al., *Plant Cell Physiol.*, 25:1353 (1984)); and (3) the vortexing method (See, Kindle, *Proc. Natl. Acad. Sci. USA*, 87:1228 (1990)).

Transformed plant cells which are derived by any of the above transformation techniques can be cultured to regenerate a whole plant which possesses the transformed genotype. Such regeneration techniques rely on manipulation of certain phytohormones in a tissue culture growth medium, typically relying on a biocide and/or herbicide marker which has been introduced together with the Mez1 or Mez2 nucleic acid. Plant regeneration from cultured protoplasts is described in Evans et al., *Protoplasts Isolation and Culture, Handbook of Plant Cell Culture*, pp. 124-176, MacMillian Publishing Company, New York, 1983; and Binding; *Regeneration of Plants, Plant Protoplasts*, pp. 21-73, CRC Press, Boca Raton, 1985. Regeneration can also be obtained from plant callus, explants, organs, or parts thereof. Such regeneration techniques are described generally in Klee et al., *Ann. Ref. of Plant Phys.* 38:467-486 (1987).

One of ordinary skill in the art will recognize that after the expression cassette is stably incorporated in transgenic plants and confirmed to be operable, it can be introduced into other plants by sexual crossing. Any of a number of standard breeding techniques can be used, depending upon the species to be crossed.

Transgenic plants containing the expression cassettes described herein can be identified by using restriction enzymes or High Performance Liquid Chromatography. Techniques for restriction enzymes and High Performance Liquid Chromatography are well known to persons skilled the art. Transgenic plants containing the expression cassettes described herein can be identified by using a Northern Blot analysis which is well known to persons skilled in the art.

Synthetic Polypeptides and Purification of Polypeptides

In addition to being produced recombinantly, the polypeptides of the present invention can also be produced synthetically, using techniques known in the art. For example, polypeptides having a length of about 50 amino acids can be synthesized using solid phase synthesis techniques, such as those described by Barany and Merrifield, *Solid-Phase Peptide Synthesis*, pp. 3-284 in *The Peptides*. Analysis, Synthesis, Biology. Vol. 2: Special Methods in Peptide Synthesis, Part A.; Merrifield et al., *J. Am. Chem. Soc.* 85:2149-2156 (1963). Polypeptides having a length greater than about 50 amino acids can be synthesized by condensation of the amino and carboxy termini of shorter fragments, a technique which is well known to persons skilled in the art.

Polypeptides of the present invention produced either recombinantly or synthetically, can be purified using standard techniques known to those persons skilled in the art, including, but not limited to, column chromatography, selective precipitation with ammonium sulfate, affinity chromatography, etc.

Methods for Repressing the Expression or Inhibiting the Repression of Expression of a Target Gene In Vivo The Mez1 and Mez2 proteins belongs to the E(z) group of Polycomb proteins. As discussed previously, it is known in the art that the esc and esc-like (homologs) proteins interact with the E(z) and E(z)-like proteins in vivo to form complexes. The E(z) and esc proteins interact with each other, but are not known to physically interact with any other characterized PcG proteins. While *C. elegans* and plants contain homologs of the proteins in the E(z)/esc complex, they do not contain the PRC1 complex. The E(z)/esc complex has been found to repress the expression of a gene during a specific developmental stage and in a specific tissue in plants and *C. elegans* which lack the PRC1 complex (see Goodrich et al, *Nature,* 386(6620):44-51 (1997), Holdeman et al., *Development,* 125(13):2457-67 (1998), Korf et al., *Development,* 125 (13):2469-78 (1998), Kelly and Fire, *Development,* 125(13): 2451-6 (1998)).

The Mez1 and Mez2 nucleic acids and of the present invention can be used for a number of useful purposes. First, the Mez1 and/or Mez2 proteins can be used in a method to repress the expression of a desired target gene in specific tissue in a plant in vivo. The gene targeted for silencing would either be in cells expressing endogenous or introduced Mez1 and/or Mez2 and ZmFIE proteins. The ZmFIE2 protein is an esc-like protein isolated from *Zea mays* L. and is described in U.S. application Ser. No. 09/906,549, filed on Jul. 16, 2001, abandoned, and entitled "Polycomb Gene from Maize—ZmFIE2," hereby incorporated by reference. The Mez1 and/or Mez2 nucleic acids and ZmFIE2 nucleic acids could be constitutively expressed in these cells or introduced into a plant containing the cells by crossing. The gene targeted for silencing may have any of a number of different promoters, but would also contain DNA sequence motifs or contexts to which the Mez1 and/or Mez2/ZmFIE2 complex is targeted. This would allow silencing of a gene in specific tissues or at specific times in development. For example, immature roots contain a non-functional Mez2 protein, but a functional ZmFIE2 protein. Therefore, these cells would not silence an introduced or endogenous gene containing DNA sequences which attract the Mez2/ZmFIE2 complex. Alternatively, developing leaf tissues contain a functional Mez2 and ZmFIE2 protein. Therefore, an introduced or endogenous gene containing DNA sequences which attract the Mez2/ZmFIE2 complex would be silenced.

Alternatively, the Mez1 and Mez2 proteins of the present invention can be used in a method to prevent the repression of a particular desired target gene in vivo in a plant. One mechanism by which this could be accomplished is by producing dominant negative mutant forms of said Mez1 and Mez2 protein which fail to form a complex with any esc or esc-like proteins. In this approach, the recombinant expression cassette encodes a mutant Mez1 and/or Mez2 polypeptide (the mutant polypeptide contain various substitutions, deletions, additions, etc.) which fails to bind to any esc or esc-like proteins properly. Thereupon, the complex would not form.

A second mechanism by which this could be accomplished is through the use of antisense RNA. In this approach, recombinant expression cassettes containing the Mez1 and/or Mez nucleic acids in the antisense direction can be inserted into a plant. Preferably, the recombinant expression cassettes contain a tissue-specific promoter which will direct expression to the tissues containing the desired target gene of interest. The antisense RNA produced by the expression cassette will hybridize with the endogenous mRNA produced from the Mez1 or Mez2 genes within the plant, thus preventing the expression of any Mez1 or Mez2 protein. Because there will be no Mez1 or Mez2 protein, the complex between the Mez1 and/or Mez2 proteins and any esc or esc-like proteins will fail to form.

The use of the Mez1 and Mez2 proteins of the present invention to repress the expression or prevent the repression of the expression of a target gene in specific tissue in a plant in vivo could be used to regulate homeotic gene expression in plants to create novel plants having improved agronomic traits (see Goodrich et al, *Nature,* 386(6620):44-51 (1997)).

The following Examples are offered by way of illustration, not limitation.

EXAMPLE 1

Cloning and Characterization of the Mez1 and Mez2 Genes

Cloning of Mez1 (SEQ ID NO: 1) and Mez2 (SEQ ID NO: 3): *Drosophila* E(z) (AAC46462) (SEQ ID NO: 24) was used in a TBLASTN search of the Pioneer Hi-Bred EST database. Two contigs with significant similarity were discovered, and named Maize E(z)-like 1 (Mez1) and Maize E(z)-like 2 (Mez2). Other contigs containing a SET domain were also present but displayed more similarity to trithorax than to E(z). The ctsbp19 clone contained the 3' 801 bp of Mez1. The Mez2 contig originating from the cbmfe16 clone contained the 3' 1144 bp of the Mez2 cDNA. To obtain full-length clones and sequence for the 5' region of both genes, Random Amplification of cDNA Ends (RACE) was performed. Additionally the 3' end of Mez1 (SEQ ID NO: 1) and Mez2 (SEQ ID NO: 3) were obtained by RACE to verify the EST sequence. RACE reactions were performed on one-week seedling Mo17 cDNA using the Marathon cDNA kit (Clontech, Palo Alto, Calif.) using Advantage2 polymerase (Clontech, Palo Alto, Calif.). The primers used were as follows: Mez1F1-GGG TGT GGT GAT GGT ACA TTG G (SEQ ID NO:7), Mez1R2-CAG CTT GTC ACC CAT TCT GTA TGC G (SEQ ID NO: 8), Mez2R3-TGC CTC GTC CTT CTT TGA TCC TTC G (SEQ ID NO: 9) and Mez2F3-CTC ACA AGG AAG CAG ACA AAC GCG G (SEQ ID NO: 10). RACE products were gel purified and cloned into pGEM-T Easy (Promega, Madison Wis.).

Sequencing: The plasmids were sequenced using BigDye terminator cycle sequencing on an ABI sequencer (Perkin-Elmer Applied Biosystems). Sequencing reactions were done in a 10 µl volume with 320 ng DNA and 10 pg of primer. Primers used were as follows: T7 (Promega), SP6 (Promega), Mez1F1 (SEQ ID NO: 7), Mez1F2-TAC CTT GGT GAG TAC ACT GGG GAA C (SEQ ID NO: 11), Mez1F4-CCA TTT CGT GTA TCA GAC CTA AGC (SEQ ID NO: 12), Mez1F5-CAT CAA CGC CCT CCA AGC (SEQ ID NO: 13), Mez1R6-TGC CAC ATT CTT GAA CTG TCA TCC G (SEQ ID NO: 14), Mez1R4-GCA CAG TGA CAT CCT CGA AAA CG (SEQ ID NO: 15), Mez1R5-GTC CCT GCT CAA TTG CC (SEQ ID NO: 16), Mez2F4-GCG GAC AAT TGT GCG GTT CG (SEQ ID NO: 17), Mez2F5-GGT TGT TCA CAG AAT TTG G (SEQ ID NO: 18), Mez2R4-CTT CCT AAC AAA ATC CTT TGC TGT TG (SEQ ID NO: 19), and Mez2R5-TTG CTC CAT GTA GTC TTG (SEQ ID NO: 20).

Sequence analysis: The sequences were assembled through the contig assembly program. Reverse complement, translation and ClustalW were all accessed from the ABCC sequence analysis page. ClustalW alignments were processed using Boxshade. All BLAST searches were performed using the NCBI BLAST feature. For some searches the advanced BLAST feature was used and a target organism was specified. Targeting signals and putative localization were predicted using PSORT. Domains were identified using SMART.

Phylogenetic analysis: The SET domains from all E(z)-like proteins were aligned using ClustalW, Thus alignment was then submitted to the PHYLIP server. The protpars feature was used with bootstrapping performed before analysis. One hundred replicates were examined to determine bootstrap values. The consensus tree was then displayed with bootstrap values.

RT-PCR analysis: Total RNA was extracted from tissues including embryo, leaf, immature ear, immature tassel, 3-day root, pollen and BMS (Black Mexican Sweet) suspension cultures using TRIzol (Life Technologies Gibco/BRL). PolyA+RNA, isolated using PolyAtract (Promega) was used to make cDNA with Marathon cDNA Amplification Kit (Clontech). 2 ng of cDNA was used in each PCR reaction. The primers used were: Mez1F1 (SEQ ID NO: 7), Mez1R1-CGG GAC CTA ACT CTA CGG ATG G (SEQ ID NO: 21), Mez2F6-CGC AGC TGA TAC GGC AAG TCC AAT CG (SEQ ID NO: 22) and Mez2R2-GTA TCA TCC GGA GCG ACT CTT CAG C (SEQ ID NO: 23). Cycling conditions were as follows: 94° 2', 5 cycles of 94° for 30", 70° for 30", 72° for 1', 5 cycles of 94° for 30", 67.5° for 30", 72° for 1', then 25 cycles of 94° for 30", 65° for 30", 72° for 1' followed by 72° for 7'. Each 25 µl reaction contained 1 µl of a 10 µM primer solution for each primer, 2 ng cDNA, 2.5 µl 10× buffer, 2 µl 25 mM MgCl 2, 0.3 µl 25 mM dNTPts (Promega), 0.2 µl Taq polymerase (Promega) and 17 µl ddH$_2$O.

Sequence analysis: The sequences were assembled through the contig assembly program. Reverse complement, translation and ClustalW were all accessed from the ABCC sequence analysis page. ClustalW alignments were processed using Boxshade. All BLAST searches were performed using the NCBI BLAST feature. For some searches the advanced BLAST feature was used and a target organism was specified. Targeting signals and putative localization were predicted using PSORT. Domains were identified using SMART.

Results

Mez1 and Mez2:

Two contigs with significant similarity to the *Drosophila* E(z) were discovered in the Pioneer-Hi-Bred EST database. These contigs were named Maize E(z)-like 1 (Mez1) and Maize E(z)-like 2 (Mez2). To test for the presence of Mez1 ESTs in the public maize database the Mez1 cDNA was used in a BLASTN search. No Mez1 ESTs were found, but two putative trithorax hits were detected due to similarity of the E(z) and trithorax SET domains.

Mez1 (SEQ ID NO: 1) was mapped to the short arm of chromosome 6 (bin 6.01-6.02). The Mez2 sequence (SEQ ID NO: 3) was placed to the short arm of chromosome 9 (bin 9.04). Mutants with the phenotypes similar to the *Arabidopsis* clf or medea have not been mapped to these regions.

Alignment of Mez1 and Mez2

The amino acid sequences of Mez1 (SEQ ID NO: 2) and Mez2 (SEQ ID NO: 4) were aligned using ClustalW (FIG. 3). The sequences are 42% identical and 56% similar over their entire lengths. The nucleotide sequences of Mez1 (SEQ ID NO: 1) and Mez2 (SEQ ID NO: 3) are 52% identical. In maize, it is common to find two closely related sequences due to the ancient tetraploid nature of maize. Often the two sequences that arose from the tetraploid fusion display greater than 70% nucleotide identity (Gaut and Doebley, PNAS, U.S.A., 94:6809-6814 (1997)). The lower identity of the Mez1 and Mez2 nucleotide sequences (SEQ ID NO: 1 and SEQ ID NO: 3, respectively) indicates that these genes were probably duplicated prior to the formation of the maize tetraploidy event. In addition, the map positions of these two sequences do not correspond to colinear regions of the maize genome (Helentjaris, T., Maize Newsletter, 69:67-81 (1995)).

Characteristics of Mez1 and Mez2:

A putative bipartite nuclear localization signal is found in both Mez1 (SEQ ID NO: 2) and Mez2 (SEQ ID NO: 4) (See, FIGS. 4 and 5). Mez2 (SEQ ID NO: 4) and Mez1 (SEQ ID NO: 2) were aligned with the other characterized E(z)-like proteins using ClustalW (FIG. 4).

There are two regions near the C-terminal of the protein that are well conserved among all E(z) proteins (FIG. 4a). These are the Cys-rich region and the SET domain. The Cys-rich region has a number of highly conserved cysteine residues. The spacing of the cysteine residues is unlike other Cys-rich zinc finger domains involved in DNA binding. The function of this domain is not known but it is highly conserved among all E(z) like genes. Mez1 (SEQ ID NO: 2) is 45% identical to E(z) in this region while Mez2 (SEQ ID NO: 4) is 46% identical. The SET (Su(var)3-9, Enhancer-of-zeste, Trithorax) domain found at the C-terminal end of the protein is also highly conserved. The SET domain of Mez1 (SEQ ID NO: 2) is 55% identical to the E(z) SET domain (Mez2 (SEQ ID NO: 4) is 54% identical). SET domains appear to be involved in mediating protein-protein interactions (Cui et al., Nat. Genet., 18:331-337 (1998); Huang et al., J. Biol. Chem., 273:15933-15939 (1998)). Interestingly, the nonspecific transcriptional activator, trithorax, also contains a SET domain indicating that SET domains alone are not responsible for transcriptional repression.

The Mez1 and Mez2 sequences (SEQ ID NO: 2 and SEQ ID NO: 4, respectively) were submitted to the SMART server to identify other domains within these proteins (Schultz et al., PNAS USA, 95:5857-5864 (1998); Schultz et al., Nucl. Acids Res., 28:231-234 (2000)). In addition to the SET domain, a SANT (SWI3, ADA2, N-CoR and TFIIIB" DNA-binding domains) domain was identified (FIGS. 4 and 5). The myb-DNA binding domain is a SANT domain as well. This indicates that plant E(z)-like genes have a domain that may facilitate DNA binding. The SMART program also predicts the presence of a SANT domain in the animal E(z)-like proteins.

An acidic region is present in E(z)-like proteins near the N-terminal region (FIGS. 4 and 5). The function of this domain is not known. This acidic region is conserved in all E(z)-like proteins. A small region near amino acid 250 of the plant E(z)-like proteins is highly conserved. This region, named CRRC region, is not recognized by the SMART program. The CRRC region is composed primarily of polar or charged residues.

Evolution of E(z) Sequences:

*Arabidopsis* contains at least three E(z)-like genes that perform distinct functions. The low degree of nucleotide similarity between Mez1 and Mez2 indicates that these genes may have distinct evolutionary origins. The SET domain sequences of all E(z)-like proteins were aligned using ClustalW. This alignment was then processed using PHYLIP and a parsimonious tree was constructed (FIG. 5). The tree shows grouping of the *Arabidopsis* clf and the maize Mez1. When the full-length protein sequences were used for the alignments, the same tree was produced. The results indicate that Mez1 is a clf-like gene in maize while Mez2 is likely an EZA1 homolog.

Alternative Splicing of Mez2

Figure 6:
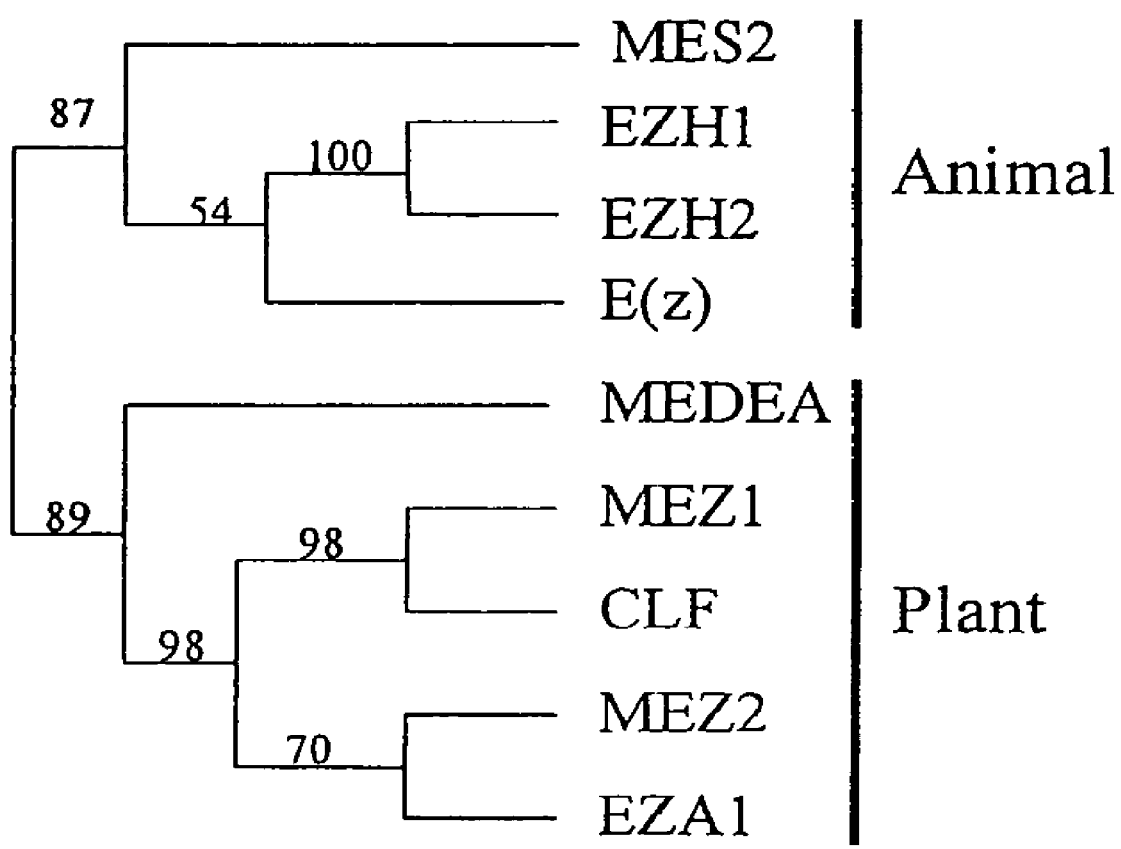
FIG. 6 shows the alignment of the SET domains from *Drosophila* E(z) (AAC46462) (SEQ ID NO: 24), human EZH1 (AAC50778) (SEQ ID NO: 25), human EZH2 (AAC51520) (SEQ ID NO: 26), *C. elegans* MES-2 (AAC27124) (SEQ ID NO: 27), *Arabidopsis* CLF (AAC23781) (SEQ ID NO: 28), *Arabidopsis* MEA (AAC39446) (SEQ ID NO: 29), *Arabidopsis* EZA1 (AAD09108) (SEQ ID NO: 30), Mez1 (SEQ ID NO: 2) and Mez2 (SEQ ID NO: 4) using ClustalW (region indicated by [ ] in FIG. 4). The *Arabidopsis* sequences are underlined. The maize sequences are in bold text. Bootstrap values are indicated by the numbers at nodes in the tree. Only nodes with bootstrap values greater than 50% are shown.

In an attempt to generate a full length Mez2 clone, PCR primers in the 5' and 3' UTR region were used to amplify B73 ear cDNA. In addition to a major product of the expected size, two smaller products were observed (FIG. 6a). These two products were excised and used for PCR reactions with primers from various regions of the gene to detect where the difference in size was arising. A region near the middle of Mez2 (SEQ ID NO: 3) was identified and the PCR products from the two isoforms, Mez2 alternative splice 1 ($Mez2^{as1}$) and Mez2 alternative splice 2 ($Mez2^{as2}$), were sequenced. Sequencing revealed that the smaller products were identical to Mez2 (SEQ ID NO: 3) except for the missing 659 base pairs in $Mez2^{as1}$ and 810 base pairs in $Mez2^{as2}$. The deleted fragment in $Mez2^{as1}$ corresponds to base pairs 1016 to basepairs 1676 of Mez2 (SEQ ID NO: 3). The $Mez2^{as1}$ deletion will cause a frameshift and a truncated protein of 341 amino acids (FIG. 6). The deletion in the $Mez2^{as2}$ corresponds to basepairs 1016 to basepairs 1827 of Mez2 (SEQ ID NO: 3) and does not result in a frameshift. The deletion in $Mez2^{as2}$ results in a 624 amino acid protein that is missing the SANT domain.

It is possible that the presence of multiple products in these PCR reactions is due to secondary structure of the RNA or aberrant PCR products. The presence of the products displaying identical size shifts in PCR reactions using multiple primers sets makes it unlikely that these are the result of mispriming events. No significant secondary structure was identified in these regions using secondary structure prediction programs. Together, these findings indicate that the presence of multiple products is most likely due to alternative splicing of Mez2 mRNA.

Expression of Mez1 and Mez2:

cDNA from various maize tissues was tested for the presence of Mez1 and Mez2 transcripts. Abundant Mez1 transcripts were detected in embryo, ear and root tissues (FIG. 7a). Transcripts were also present in leaf, BMS cell culture, and pollen tissues. There were no tissues tested that did not contain Mez1 transcripts.

The same tissues were tested for the presence of Mez2 transcripts (FIG. 7b). The primers used to test for Mez2 expression flank the site of alternative splicing documented in cDNA ear tissue. Amplification from ear cDNA revealed the presence of the three transcripts observed previously. In the lane amplified from embryo cDNA, a doublet of $Mez2^{as2}$ and a smaller fragment is observed. The sequence of this smaller fragment has not been analyzed. No Mez2 or $Mez2^{as1}$ transcripts are observed in embryo tissue. Mez2 transcripts are the predominant form in leaf tissue, with very faint $Mez2^{as1}$ and $Mez2^{as2}$ products. An intense Mez2 product is amplified from immature tassel cDNA. In addition, a $Mez2^{as2}$ and two uncharacterized products are present. Only $Mez2^{as1}$ transcripts are detected in 3-day root cDNA. Faint Mez2 and $Mez2^{as2}$ products are observed from the BMS cell culture cDNA.

Mutator Insertions into Mez2:

The Mez1 and Mez2 sequences (SEQ ID NO: 1 and SEQ ID NO: 3, respectively) were submitted to the Pioneer Hi-Bred Int'l TUSC system. The TUSC system is designed to find Mutator (Mu) insertions in a sequence of interest. Difficulties were encountered in designing primers to amplify the Mez1 sequence (SEQ ID NO: 1). Mez2 primers were designed and used to screen the DNA pools. Four independent insertions were found. The location of the four Mu insertions and five of the Mez2 introns are shown in FIG. 2a. Mez2-Mu1 is an intron insertion while Mez2-Mu2, Mez2-Mu3 and Mez2-Mu4 are all exon insertions.

All references, patents and patent applications referred to herein are hereby incorporated by reference.

The present invention is illustrated by way of the foregoing description and examples. The foregoing description is intended as a non-limiting illustration, since many variations will become apparent to those skilled in the art in view thereof. It is intended that all such variations within the scope and spirit of the appended claims be embraced thereby.

Changes can be made to the composition, operation and arrangement of the method of the present invention described herein without departing from the concept and scope of the invention as defined in the following claims.

What is claimed is:

1. An isolated and purified nucleic acid for repressing the expression of or inhibiting the repression of a target gene comprising a polynucleotide selected from the group consisting of SEQ ID NO: 3 and a polynucleotide that encodes SEQ ID NO: 4.

2. An expression cassette comprising a promoter sequence operably linked the nucleic acid of claim 1.

3. The expression cassette of claim 2 further comprising a polyadenylation signal operably linked to the nucleic acid.

4. The expression cassette of claim 2 wherein the promoter is a constitutive or tissue specific promoter.

5. A bacterial cell comprising the expression cassette of claim 2.

6. The bacterial cell of claim 5 wherein the bacterial cell is an *Agrobacterium tumefaciens* cell or an *Agrobacterium rhizogenes* cell.

7. A plant cell transformed with the expression cassette of claim 2.

8. A transformed plant containing the plant cell of claim 7.

9. The transformed plant of claim 8 wherein the plant is *Zea mays*.

10. A seed that contains the expression cassette of claim 2.

11. A transformed seed from the transformed plant of claim 8.

* * * * *

UNITED STATES PATENT AND TRADEMARK OFFICE
CERTIFICATE OF CORRECTION

| | | |
|---|---|---|
| PATENT NO. | : 7,626,078 B2 | Page 1 of 1 |
| APPLICATION NO. | : 12/013464 | |
| DATED | : December 1, 2009 | |
| INVENTOR(S) | : Shawn M. Kaeppler et al. | |

It is certified that error appears in the above-identified patent and that said Letters Patent is hereby corrected as shown below:

Title page, immediately below the list of inventors, please insert the following language:

-- This invention was made with United States government support awarded by the following agencies: US Department of Agriculture USDA/CSREES 00-CRHF-0-6055. The United States government has certain rights in this invention. --

Signed and Sealed this

Sixteenth Day of November, 2010

David J. Kappos
*Director of the United States Patent and Trademark Office*